United States Patent
Castiel et al.

(10) Patent No.: US 9,265,719 B2
(45) Date of Patent: Feb. 23, 2016

(54) COSMETIC USE OF MICROORGANISM(S) FOR THE TREATMENT OF SCALP DISORDERS

(75) Inventors: Isabelle Castiel, Nice (FR); Audrey Gueniche, Rueil Malmaison (FR)

(73) Assignees: L'OREAL, Paris (FR); NESTEC SA, Vevey (CH)

( * ) Notice: Subject to any disclaimer, the term of this patent is extended or adjusted under 35 U.S.C. 154(b) by 0 days.

(21) Appl. No.: 12/659,597

(22) Filed: Mar. 15, 2010

(65) Prior Publication Data

US 2011/0014248 A1 Jan. 20, 2011

Related U.S. Application Data

(63) Continuation of application No. 12/509,756, filed on Jul. 27, 2009, now abandoned.

(60) Provisional application No. 61/084,582, filed on Jul. 29, 2008, provisional application No. 61/213,517, filed on Jun. 16, 2009.

(51) Int. Cl.

| | | |
|---|---|---|
| A61K 8/02 | (2006.01) | |
| A61K 8/99 | (2006.01) | |
| A61K 35/74 | (2015.01) | |
| A61K 9/68 | (2006.01) | |
| A61K 9/00 | (2006.01) | |
| A61K 9/48 | (2006.01) | |
| A61K 9/28 | (2006.01) | |
| A61P 17/14 | (2006.01) | |
| A61Q 5/02 | (2006.01) | |
| A61Q 5/06 | (2006.01) | |
| A61Q 5/10 | (2006.01) | |
| A61Q 5/12 | (2006.01) | |
| A61Q 11/00 | (2006.01) | |
| A61Q 5/00 | (2006.01) | |
| A61Q 19/00 | (2006.01) | |

(52) U.S. Cl.
CPC ............... *A61K 8/99* (2013.01); *A61K 8/0216* (2013.01); *A61K 8/0229* (2013.01); *A61Q 5/006* (2013.01); *A61Q 19/00* (2013.01); *A61K 2800/88* (2013.01); *A61K 2800/92* (2013.01)

(58) Field of Classification Search
CPC ... A61Q 5/006; A61Q 19/00; A61K 2800/88; A61K 2800/92; A61K 8/99; A61K 8/0229; A61K 8/0216

See application file for complete search history.

(56) References Cited

U.S. PATENT DOCUMENTS

| | | | | |
|---|---|---|---|---|
| 2002/0102228 | A1* | 8/2002 | Dunlop et al. | 424/70.1 |
| 2006/0171936 | A1* | 8/2006 | Gueniche et al. | 424/93.45 |
| 2006/0246149 | A1* | 11/2006 | Buchholz et al. | 424/603 |
| 2010/0272839 | A1 | 10/2010 | Gueniche et al. | |
| 2010/0278793 | A1 | 11/2010 | Gueniche et al. | |

FOREIGN PATENT DOCUMENTS

WO WO 2005/030230 * 4/2005

OTHER PUBLICATIONS

Pierard-Franchimont et al. International Journal of Cosmetic Science, 2002, 24, 249-256.*
Gupta et al. J. Am. Acad. Dermatol. 2004, 51 (5), 785-798.*
Kragballe, Curr. Probl. Dermatol. 2009, 38, 16-171 (abstract only).*
Essence product data sheet.*
Gupta et al. J. Am. Acad. Dermatol. 51 (5), 2004, 785-798.*
Piérard-Franchimont et al. Int J Cosmet Sci, 2002, 24 (5), 249-256; of record.*
Kragballe Curr. Probl. Dermatol. 2009, 38, 160-171; Abstract only; of record.*
Elemence (of record).*
Collins English Dictionary (entry: scalp), 2013.*
U.S. Appl. No. 12/607,142, filed Oct. 28, 2009, Gueniche, et al.
U.S. Appl. No. 13/056,344, filed Jan. 28, 2011, Castiel, et al.
U.S. Appl. No. 12/509,756, filed Jul. 27, 2009, Castiel, et al.

\* cited by examiner

*Primary Examiner* — Ali Soroush
*Assistant Examiner* — Genevieve S Alley
(74) *Attorney, Agent, or Firm* — Oblon, McClelland, Maier & Neustadt, L.L.P.

(57) ABSTRACT

The present invention relates to a use of an effective amount of at least one probiotic microorganism and/or a fraction thereof and/or a metabolite thereof for preventing and/or treating dandruff disorders of the scalp, as well as a cosmetic process for preventing and/or treating a dandruff condition including the administration a first cosmetic active agent and of at least a second cosmetic active agent, topically, the said first and second cosmetic active agents being formulated in separate compositions, the first cosmetic active agent being chosen from probiotic microorganisms, and mixtures thereof, and the second cosmetic active agent being chosen from antidandruff active agents.

27 Claims, 4 Drawing Sheets

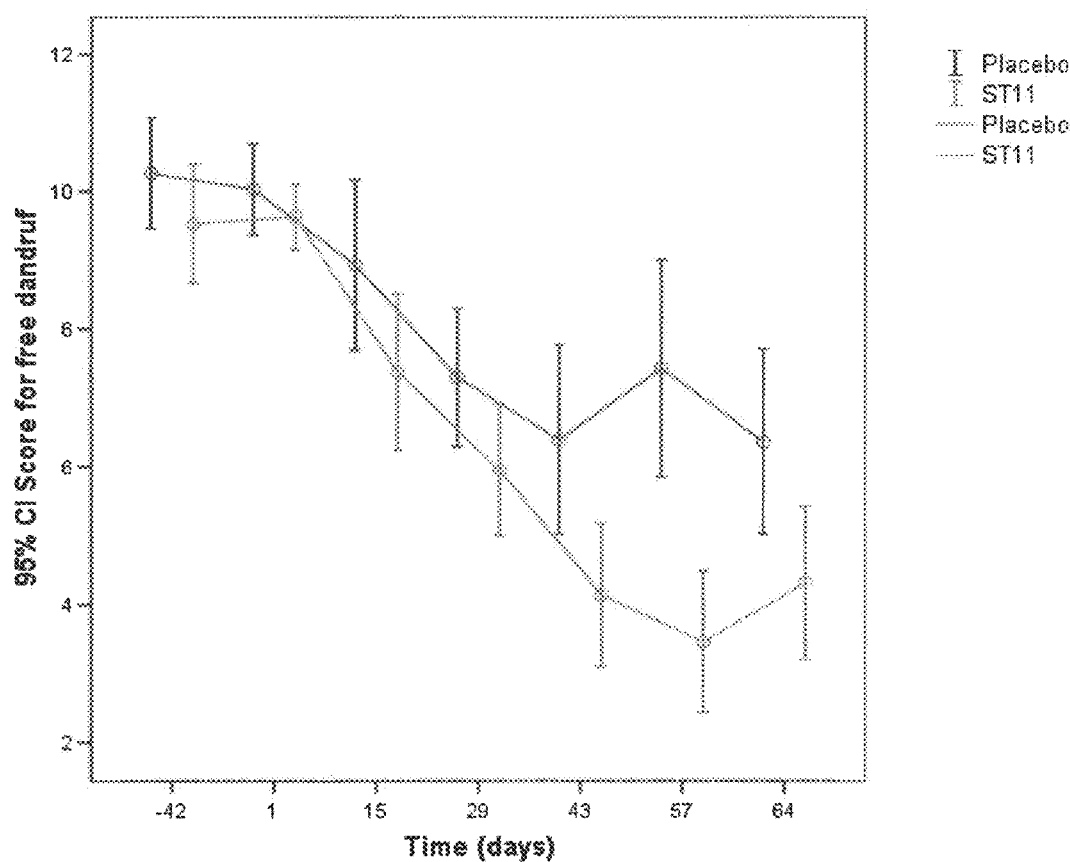
Fig. 1 : Evolution of scores for free dandruff over time (in days)
(Results expressed as mean and mean confidence interval)

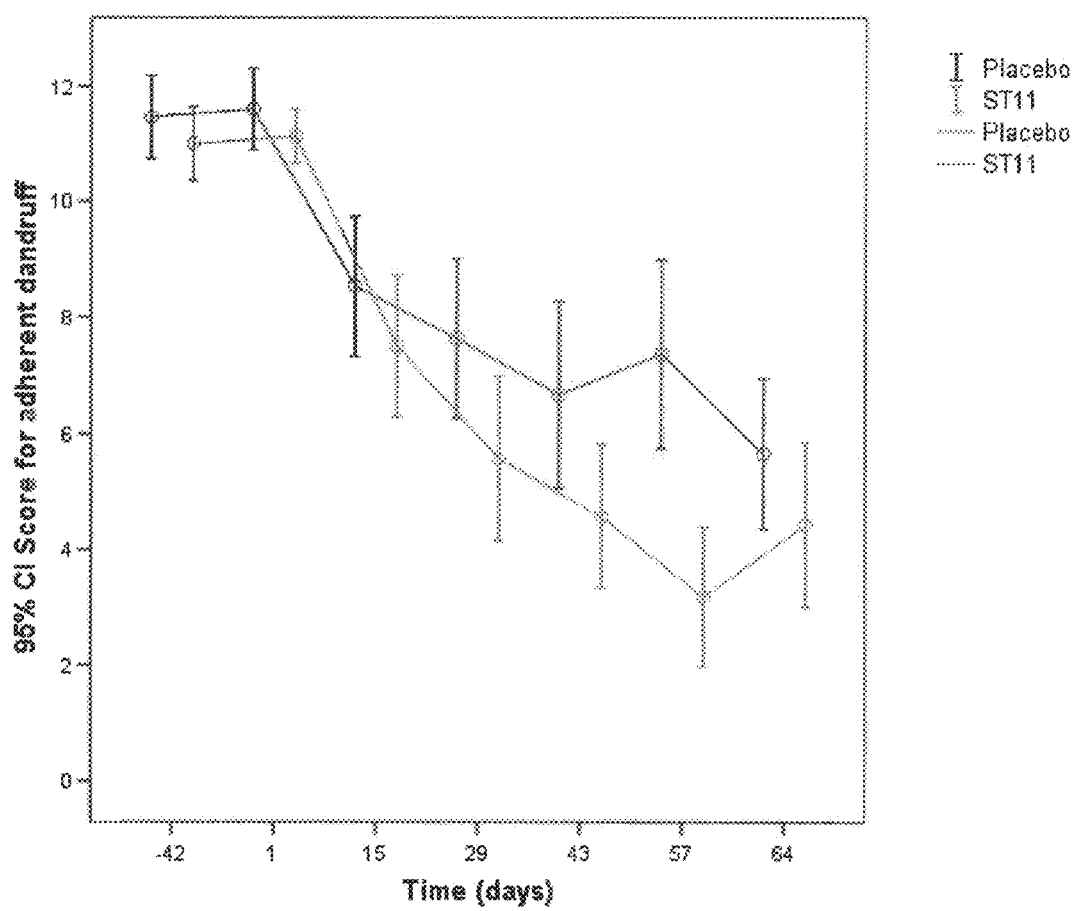
Fig. 2: Evolution of scores for adherent dandruff over time (in days)
(Results expressed as mean and mean confidence interval)

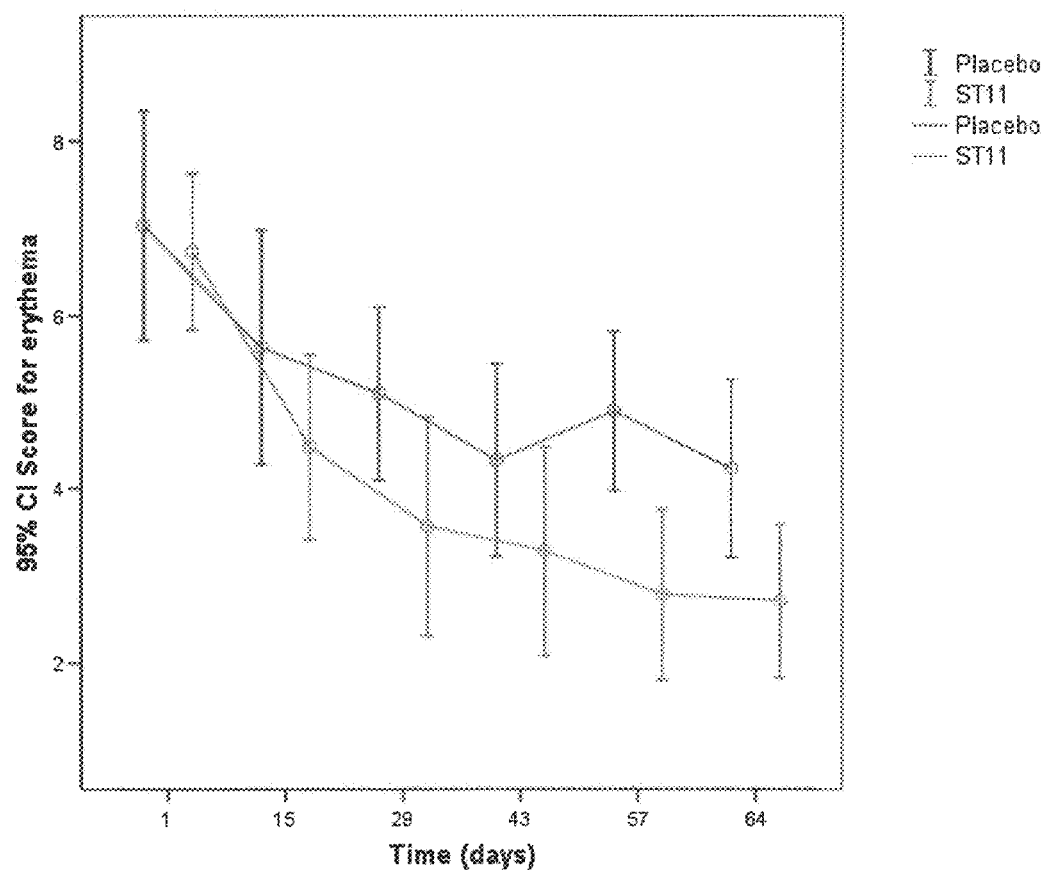
Fig. 3: Evolution of scores for erythema over time (in days)
(Results expressed as mean and mean confidence interval)

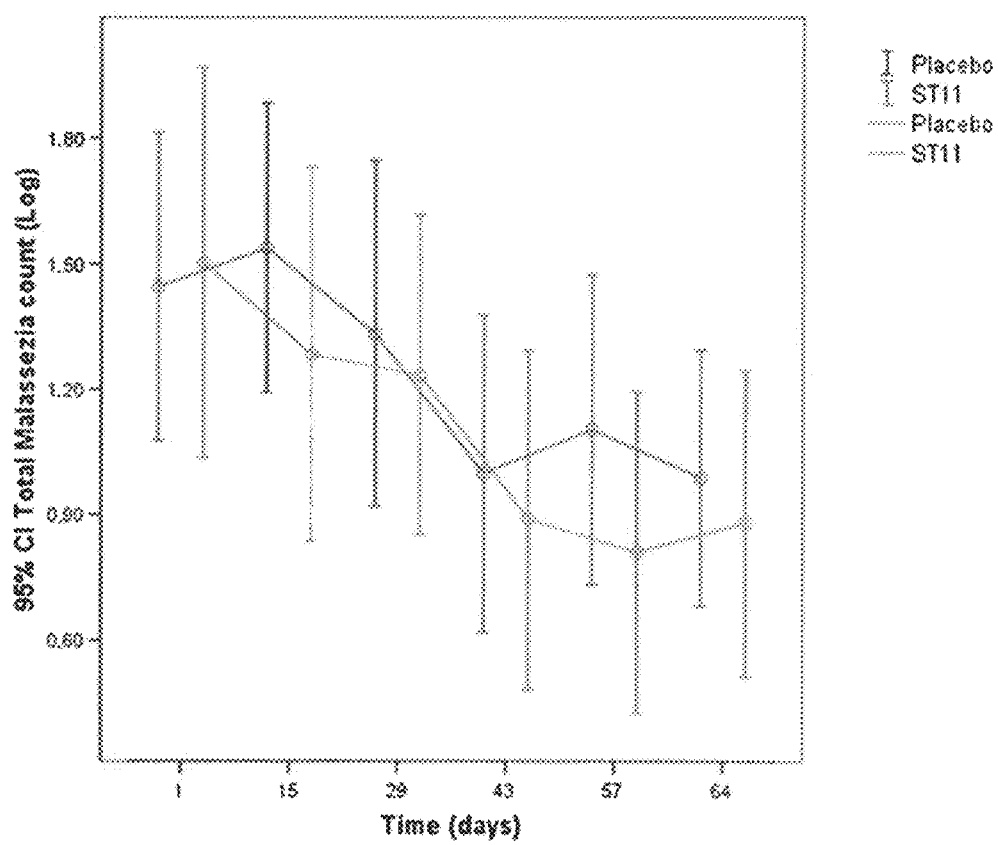
Fig. 4: Total *Malassezia* count over time (in days)
(Results expressed as mean and mean confidence interval)

COSMETIC USE OF MICROORGANISM(S) FOR THE TREATMENT OF SCALP DISORDERS

CROSS REFERENCE TO RELATED APPLICATIONS

This application in a Continuation of U.S. application Ser. No. 12/509,756, filed Jul. 27, 2009, and claims priority to French Patent Applications No. 08 57865, filed Nov. 19, 2008, and No. 09 53611, filed Jun. 2, 2009, and U.S. Provisional Patent Applications No. 61/084,582, filed Jul. 29, 2008, and No. 61/213,517, filed Jun. 16, 2009, the disclosures of which are incorporated herein by reference in their entireties.

BACKGROUND OF THE INVENTION

1. Field of the Invention

The present invention aims principally to propose a new active agent for the prevention and/or treatment of scalp disorders, especially aesthetic disorders. In particular, the present invention relates to dandruff disorders of the scalp, in particular of a greasy scalp. The present invention is also directed towards proposing a novel cosmetic process for preventing and/or treating a dandruff condition of the scalp. The present invention also relates to an assembly or kit that is suitable for use in a process of the invention. The present invention also relates to the field of topical products, food supplements or functional foods intended for scalp care.

2. Discussion of the Background

The scalp is an epidermis that undergoes continual renewal, like the rest of the cutaneous tissue, and that is rich in sebaceous glands. Normally, the scalp is renewed by imperceptible, non-visible elimination of the superficial skin cells. However, excessive renewal of the cells of the stratum corneum of the scalp, for various reasons, may result in the formation of large, thick patches of cells which are visible to the naked eye, known as "dandruff".

Various factors may promote the onset of dandruff. For example, mention may be made of stress, the winter period, an excess of sebum, a hydration defect or colonization of the skin or of the hair follicles by yeasts of the *Malassezia* spp. type. These factors especially have the common feature of causing or promoting skin inflammation. Such an inflammation reinforces the appearance or even increases the presence of dandruff.

The *Malassezia* sp. genus is constituted of lipophilic yeast normally present on human skin and on the skin of certain warm-blooded animals. The distribution thereof depends on age, on sebaceous gland activity and on certain pathologies. The *Malassezia* sp. yeast represents approximately 45% of the normal commensal flora at the surface of the scalp in individuals without dandruff, but can represent 75% of the flora in the case of dandruff, and up to 85% in the case of associated seborrhoeic dermatitis. The other microorganisms present at the surface of the scalp are micrococci and *Propionobacterium*. Imbalance of the scalp ecoflora is a factor that promotes or even reinforces the presence of dandruff.

Dandruff conditions are chronic, frequent, recurring conditions that are socially incapacitating owing to their obvious unattractive nature. Many factors can amplify these phenomena and result in the appearance of additional disorders, such as inflammatory conditions of the scalp. These dandruff conditions and/or inflammatory conditions of the scalp are reflected by an impairment of the barrier function of the epidermis. What is more, these conditions may give rise to sensations of itching or pruritus, resulting in scratching behaviour which amplifies the phenomenon of appearance of the dandruff.

The dandruff conditions of the scalp may be of greasy or oily type or of dry type.

The dry dandruff conditions of the scalp are more frequently manifested and are amplified during skin hydration disorders, and especially during substantial dryness of the epidermis of the scalp. Thus, the treatment of dry dandruff conditions, and the solving of the unattractive manifestations thereof, involve being able to sufficiently rehydrate the scalp.

Besides, as indicated above, the scalp is rich in sebaceous glands. It has been observed that dandruff develops more easily in the excessive presence of sebum and is more readily pruritic. Sebum secretion is a normal phenomenon which is useful for the skin and for the head of hair. Sebum protects the scalp and gives the hair a sheen by lubricating the cuticle. However, hypersecretion of sebum, or seborrhoea, may lead to disruptions, annoyances, sensations or feelings of discomfort, aesthetic disorders, or even a skin pathology. Thus, an excessive secretion of sebum promotes the appearance of a greasy or oily dandruff condition of the scalp or greasy or oily dandruff.

It has also been recently demonstrated that yeast of *Malassezia* type have a substantial lipase activity, resulting in the hydrolysis of sebum triglycerides so as to give fatty acids. These fatty acids are then capable of causing dandruff conditions in sensitive individuals, i.e. individuals having an impaired barrier function, and therefore more particularly susceptible to the destructive action of fatty acids on the cutaneous barrier.

Thus, the greater the presence of sebum, the more readily oily dandruff develops. Moreover, it has a tendency to be more readily pruritic.

Dandruff conditions generally respond to various local or systemic treatments. For example, various preparations comprising antimicrobial agents or keratolytic agents or keratinization regulators are commonly proposed for treating dandruff conditions. In particular, preparations combining antifungal and anti-seborrhoeic agents have been proposed in order to treat severe dandruff conditions, in particular greasy or oily dandruff conditions. The antifungal-based treatments demonstrate certain effectiveness on oily dandruff conditions.

However, the efficacy of these treatments is only suspensory and demands rigorous adherence on the part of the user (frequency of use and sufficient application time). Now, daily and long-term use of these treatments may lead to a phenomenon of dependence that reduces their efficacy. The dependence may be associated with a rebound phenomenon occurring when the treatment is stopped. The rebound phenomenon is generally manifested by hyperseborrhoea or pruritus, which are paradoxically liable to worsen the dandruff condition by impairing the barrier function of the scalp.

Moreover, the aggressiveness of certain antidandruff active agents with respect to the epidermal cells or the scalp ecoflora may also affect the scalp's barrier functions and lead to worsening of the dandruff condition.

Unpleasant side effects, such as heating or irritation phenomena, may also be manifested during the use of these treatments. These side effects may also be reflected by poor adherence to the treatments, thus reducing their efficacy.

In addition, most of the active agents usually used for treating dandruff often have an unpleasant odour that also reduces the adherence to the treatment.

Finally, the efficacy of antidandruff treatments is often slow to develop and requires rigorous application over the long term. This lag time often leads to failure to follow the treatment.

Consequently, many failures occur in the use of these treatments and can usually be attributed to the following factors: protocol not properly followed; frequency of use not adhered to; non-cosmetic appearance of the product; irritation by the washing base; application time not properly adhered to; lassitude.

SUMMARY OF THE INVENTION

There remains therefore a need to have new active agents capable of exerting a beneficial cosmetic or therapeutic action on scalp conditions.

There also remains a need to have active agents for re-establishing the ecoflora of the scalp, and in particular for preventing excessive colonization of the scalp by *Malassezia* sp.

There also exists a need to have new compositions which are effective for preventing and/or treating oily or dry scalp conditions, and which are pleasant and comfortable to use, thus promoting compliance with the treatment.

There also exists a need to have new active agents for preventing and/or treating pruritic conditions and seborrhoeic dermatitis of the scalp.

There also exists a need to have new active agents for preventing and/or treating inflammatory conditions of the scalp.

There also exists a need to have new active agents for hydrating the scalp, and for reinforcing its barrier-function properties.

There is also still a need for novel cosmetic treatments for preventing, reducing and/or treating dandruff conditions of the scalp, which are efficient and free of side effects liable to adversely affect good compliance.

There is also a need for a treatment for dandruff conditions of the scalp whose efficacy is manifested rapidly and durably over time.

There is also a need for a treatment for dandruff conditions of the scalp that is more efficient than the existing treatments.

There is also a need for a treatment for dandruff conditions of the scalp that does not adversely affect the ecoflora of the scalp, or even that reinforces the presence of a healthy ecoflora.

There is also a need for a treatment for dandruff conditions that is capable of maintaining, or even reinforcing, the hydration of the scalp.

There is a need for a treatment for dandruff conditions that is capable of maintaining, or even reinforcing, the barrier properties of the scalp.

There is a need for treatments for dandruff conditions that are free of the abovementioned side effects, and in particular that do not induce hyperseborrhoea, seborrhoeic dermatitis or pruriginous conditions.

There is also a need for a treatment for dandruff conditions that does not induce inflammation.

Finally, there is still a need for a treatment for dandruff conditions that is efficient and simple, and that can be performed in a prolonged or repeated manner without worsening the dandruff condition.

The object of the present invention is to satisfy these needs.

Thus, according to one object, the invention relates to the cosmetic use of an effective amount of at least one probiotic microorganism, in particular of the *Lactobacillus* sp. and/or *Bifidobacterium* sp. genus, of a fraction thereof and/or of a metabolite thereof, as an agent for preventing and/or treating scalp disorders, and in particular dandruff conditions of the scalp.

According to another of its aspects, a subject of the invention is a method, in particular a cosmetic method, for treating and/or preventing aesthetic disorders of the scalp in an individual, comprising at least one step of administering, to said individual, at least an effective amount of at least one probiotic microorganism, in particular of the *Lactobacillus* and/or *Bifidobacterium* sp. genus, and/or a fraction thereof, and/or a metabolite thereof.

A method of the invention is in particular advantageously implemented in individuals having a dandruff condition of the scalp.

A cosmetic treatment method of the invention may be implemented in particular by administering a cosmetic and/or dermatological composition or combination of the invention, according to the customary technique for using these compositions. For example: applications of creams, gels, sera, lotions, milks for removing make-up or of aftersun compositions to the keratin material such as the skin or dry hair, application of a hair lotion to wet hair or of shampoos, as regards topical application.

A cosmetic method according to the invention may thus be implemented by topical, for example daily, administration of a composition under consideration according to the invention.

A method according to the invention may comprise a single administration. According to another embodiment, the administration is repeated, for example, 2 to 3 times daily for one day or more, and generally for a sustained period of at least 4 weeks, or even 4 to 15 weeks, with, where appropriate, one or more periods of interruption.

Thus, according to another subject, the invention relates to a cosmetic process for preventing and/or treating a dandruff condition of the scalp, the said process comprising the administration of an effective amount of at least a first cosmetic active agent over a first and second consecutive periods of time, the said periods of time together forming a sequence, and of at least a second cosmetic active agent, topically, over a single period of time chosen from the first and the second period of time, the said first and second cosmetic active agents being formulated in separate compositions, the first cosmetic active agent being chosen from probiotic microorganisms, a fraction thereof and/or a metabolite thereof, and mixtures thereof, and the second cosmetic active agent being chosen from antidandruff active agents.

Unexpectedly, the inventors have observed that a probiotic microorganism, in particular of the *Lactobacillus* sp. and/or *Bifidobacterium* sp. genus, makes it possible to reduce dandruff conditions by acting on the hydration and on the barrier function of the scalp.

The use of such a microorganism promotes optimization of the assimilation of the nutrients provided by the diet, at the level of the intestinal mucosa, and contributes to promoting the provision of nutrients essential to cell metabolism and to the synthesis of the various functional and structural elements of the skin.

Thus, the reinforcement of the barrier functions of the skin makes it possible to reduce the inflammatory conditions of the skin, to maintain a balanced barrier and the integrity thereof, and to preserve a balanced ecoflora.

The scalp is then less irritated and pruriginous, less fragile and more hydrated, and the dandruff conditions are reduced.

Also, unexpectedly, the inventors have observed that the administration over a period of time of a probiotic microorganism, especially of the genus *Lactobacillus* sp., and in particular *Lactobacillus paracasei*, especially orally, with an antidandruff active agent topically, especially zinc pyrithione, this administration being preceded or followed, and in particular followed, by the administration, over another period of time, of the probiotic microorganism, in the absence of the antidandruff active agent, makes it possible to efficiently reduce dandruff conditions of the scalp without manifestation of side effects, such as pruriginous conditions, seborrhoeic dermatitis or inflammation.

The efficacy of this treatment is manifested more quickly, and more intensely, compared with the isolated use of these cosmetic active agents.

Also, the administration over a period of time of a probiotic microorganism, especially orally, with, as topical antidandruff active agent, another probiotic microorganism, this administration being preceded or followed by the administration over another period of time of the first probiotic microorganism in the absence of the antidandruff active agent, makes it possible to accelerate the establishment of the beneficial effects of the antidandruff treatment and to increase, or even amplify, the intensity of its effects.

The inventors have especially observed that after a treatment of the invention, the presence of dandruff is greatly reduced, or even nonexistent, and that the scalp's barrier properties are reinforced.

Thus, surprisingly, the oral administration of probiotic microorganisms, in particular lactic acid probiotic microorganisms, promoting the assimilation of nutrients that are essential for cell metabolism by the intestinal mucosae, is capable of remotely preventing the deleterious effects of topically applied antidandruff active agents and of reinforcing their efficacy, or even of giving rise to a synergistic effect on the prevention, reduction and/or treatment of dandruff.

The surprising effect of the process according to the invention results from the use, for the first time by the inventors, of two treatment steps, i.e. a first step including the administration, over a period of time, of a probiotic microorganism and an antidandruff active agent, this agent being administered topically, followed or preceded, in particular followed, by a second step including the administration, over another period of time, of the probiotic microorganism in the absence of the antidandruff active agent.

Such a sequence of steps makes it possible advantageously to substantially reduce, or even to eliminate, the side effects of antidandruff active agents while at the same time reinforcing the beneficial effects of the probiotic microorganism on the barrier properties of the scalp.

The protection and reinforcement of the barrier properties of the scalp allow a reduction of the skin inflammation, the maintenance of a balanced barrier, integrity of the barrier and conservation of a balanced ecoflora.

The scalp is less irritated and pruriginous, less fragile and more hydrated, and the level of dandruff is reduced.

Such a sequence of steps also makes it possible to accelerate the onset of efficacy of the antidandruff treatment and to amplify the intensity of its beneficial effects.

The administration of a probiotic microorganism alone for maintaining or improving the condition of skin or animal fur (WO 01/17365) or, where appropriate, in combination with the topical administration of an associated cosmetic active agent to improve the appearance of skin tissues (WO 2006/104 730) has been proposed.

Advantageously, the use of probiotic microorganisms according to the invention, especially of the *Lactobacillus* and/or *Bifidobacterium* sp. genus, and in particular the *Lactobacillus paracasei* ST11 strain, a fraction thereof and/or a metabolite thereof, makes it possible to restore a healthy scalp, in perfect homeostasis, and to re-establish a balanced ecoflora.

A composition of the invention may advantageously make it possible to re-establish a balanced ecoflora via the induction of epidermal defence proteins.

According to another advantage, a use according to the invention may reduce and/or treat pruritis of the scalp subsequent to the presence of irritant metabolites resulting from sebum lipid metabolism by *Malassezia* sp.

According to another advantage, a process or a use according to the invention may promote hydration and maintenance of the integrity of the scalp.

Also, advantageously, a process of the invention makes it possible to reduce the period of application of antidandruff active agents the risk of side effects arising, while at the same time maintaining or even reinforcing their activity.

A process of the invention advantageously makes it possible to accelerate the establishment of the beneficial effects of the antidandruff treatment to amplify their intensity.

A process of the invention also advantageously makes it possible to restore a healthy scalp, in perfect homeostasis, and to re-establish a balanced ecoflora.

According to another advantage, a process according to the invention makes it possible to reduce and/or treat scalp pruritus following the use of irritant antidandruff active agents.

According to another of its aspects, the present invention relates to the use of an effective amount of at least one probiotic microorganism, in particular of the *Lactobacillus* sp. and/or *Bifidobacterium* sp. genus, and/or a fraction thereof and/or a metabolite thereof, for preparing a pharmaceutical or dermatological composition for preventing and/or treating inflammation of the scalp.

The pharmaceutical or dermatological composition is prepared by admixing said at least one probiotic microorganism with at least one pharmaceutical or dermatological excipient.

In particular, such a composition is found to be effective for treating conditions of dryness or xerosis of the scalp, pruritis of the scalp or seborrhoeic dermatitis of the scalp.

A composition of the invention can advantageously be used for preventing and/or treating skin infections, and in particular of the scalp, by *Malassezia* sp.

A use in accordance with the invention may also comprise the use of at least an effective amount of at least a first probiotic microorganism, in particular of the *Lactobacillus* or *Bifidobacterium* sp. genus, and/or a fraction thereof, and/or a metabolite thereof, in combination with an effective amount of at least a second microorganism, in particular a probiotic microorganism, distinct from said first probiotic microorganism.

For the purpose of the invention, the expression "distinct from said first probiotic microorganism" means that it is possible to distinguish, in the composition, either two different microorganisms, or two different forms of the same microorganism. Thus, when the second microorganism is, for example, of the *Lactobacillus* or *Bifidobacterium* sp. genus and corresponds to the same species as that of the invention, this second microorganism is then present in a form other than the first microorganism.

According to another of its aspects, the present invention relates to a cosmetic and/or dermatological composition that is of use for preventing and/or treating scalp disorders, in particular oily dandruff conditions of the scalp, comprising, in a physiologically acceptable carrier, at least an effective amount of at least one probiotic microorganism, in particular of the *Lactobacillus* sp. and/or *Bifidobacterium* sp. genus, and/or a fraction thereof and/or a metabolite thereof, in combination with an effective amount of at least one active agent chosen from an antiseborrhoeic active agent, a hydrating active agent and an antidandruff active agent, and mixtures thereof, in particular as described hereinafter.

According to one variant embodiment of the invention, a microorganism according to the invention may be used orally.

According to another variant embodiment of the invention, the microorganism according to the invention may be used topically.

As specified hereinafter, the compositions containing a microorganism according to the invention are formulated so as to be compatible with the selected method of administration.

The invention relates to the use of a microorganism in accordance with the invention in the form of a cosmetic or dermatological or pharmaceutical composition.

According to another embodiment, in a process of the invention the first cosmetic active agent is administered orally or topically, and in particular orally.

According to another embodiment, in a process of the invention the second cosmetic active agent is preferably administered over the first period of time.

According to another embodiment, a process according to the invention may advantageously be suitable for preventing and/or treating a dandruff condition of the scalp associated with dryness or xerosis of the scalp, hyperseborrhoea of the scalp, an imbalanced ecoflora, pruritus, inflammation of the scalp, or an imbalanced barrier function of the scalp.

According to another of its aspects, the present invention relates to a cosmetic assembly comprising at least a first and a second cosmetic composition, the first composition comprising at least an effective amount of at least a first cosmetic active agent, the said first cosmetic active agent being *Lactobacillus paracasei*, a fraction thereof and/or a metabolite thereof, and the second composition comprising at least an effective amount of at least a second cosmetic active agent chosen from antidandruff active agents and being administered topically.

According to another of its aspects, a subject of the invention is a cosmetic use of at least an effective amount of at least a first and a second cosmetic active agent, the said first cosmetic active agent being *Lactobacillus paracasei*, a fraction thereof and/or a metabolite thereof, and the second active agent being chosen from antidandruff active agents and being administered topically, for preventing and/or treating a dandruff condition of the scalp.

The first and second cosmetic active agents are each formulated in a first and second cosmetic composition that are different from each other.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 illustrates the clinical evaluation of the presence of loose dandruff in individuals treated with Maltodextrin (A) or $1 \times 10^9$ cfu/g *Lactobacillus paracasei* ST11 (CNCM I-2116) (B);

FIG. 2 illustrates the clinical evaluation of the presence of adherent dandruff in individuals treated with Maltodextrin (A) or $1 \times 10^9$ cfu/g *Lactobacillus paracasei* ST11 (CNCM I-2116) (B);

FIG. 3 illustrates the clinical evaluation of erythema in individuals treated with Maltodextrin (A) or $1 \times 10^9$ cfu/g *Lactobacillus paracasei* ST11 (CNCM I-2116) (B); and FIG. 4 illustrates the results of measuring the presence of the yeast *Malassezia* sp. in individuals treated with Maltodextrin (A) or $1 \times 10^9$ cfu/g *Lactobacillus paracasei* ST11 (CNCM I-2116) (B).

DETAILED DESCRIPTION OF THE PREFERRED EMBODIMENTS

For the purpose of the present invention, the term "effective amount" is intended to mean an amount sufficient to obtain the expected effect, namely, in particular, the prevention, reduction and/or treatment of dandruff conditions.

For the purposes of the present invention, the terms "prevent" or "preventing" mean totally eliminating or partially reducing the risk of manifestation of a given phenomenon, i.e. in the present invention the presence of dandruff. "Partial reduction" implies that the risk remains but to a lesser degree than before the implementation of the invention.

Dandruff Conditions

As indicated previously, a scalp presenting excessive dryness or excessive secretion of sebum may manifest a dandruff condition, which, depending on the case, may be characterized by the presence of dry or greasy or oily dandruff, or even pruritis and/or an inflammation of the epidermis.

Dry dandruff conditions reflect a xerosis of the scalp, which may be combined with excessively rapid renewal of its stratum corneum. Dry dandruff flakes are generally in the form of small and white or grey, and are spread over the scalp and on the clothing, giving rise to an unaesthetic visual effect.

The itching associated with dryness of the scalp may lead to erythema, pruritus or even inflammation.

Greasy or oily dandruff conditions are one of the forms of seborrhoeic dermatitis.

Individuals suffering therefrom have an erythematous scalp covered with large, greasy or oily, yellow scales which accumulate so as to form packets. They have a pruritic scalp, and often have burning sensations on the affected areas.

These phenomena may be amplified by the presence of pathogenic microorganisms, especially *Malassezia* sp. These microorganisms having the property of releasing fatty acids from the sebum may impair the barrier function of the epidermis and give rise to inflammation.

During dandruff conditions of the scalp, the cutaneous barrier is unbalanced, its integrity and its hydration are impaired, and its ecoflora is disturbed. The skin of the scalp is irritated and pruritic, brittle, less hydrated, and sensitive to infections.

The use of a probiotic microorganism, in particular of the *Lactobacillus* and/or *Bifidobacterium* sp. genus, in accordance with the invention results in the hydration and the ecoflora of the scalp being re-established and in the pruritis of the scalp being decreased.

The use of a probiotic microorganism in accordance with the invention via the oral route with an antidandruff active agent via the topical route, especially over two periods of time as defined hereinbelow, leads to re-establishment of the hydration and of the ecoflora and to a decrease in the pruritus of the scalp.

This decrease is reflected by a reduction in the phases of scratching the scalp and a reduction in the impairment of the barrier function resulting therefrom. In addition, the efficacy of the treatment is markedly improved and is developed much more quickly.

The skin is then less irritated and less pruritic and the presence of the dandruff is reduced, or even eliminated.

The uses, processes and compositions according to the invention thus prove to be most particularly effective:

for preventing and/or treating scalp disorders, in particular aesthetic disorders, associated with excessive dryness, or even xerosis, for preventing and/or treating scalp disorders, in particular aesthetic disorders, associated with excess sebum excretion and/or secretion, for preventing and/or treating dandruff conditions, whether they are dry or greasy or oily, of the scalp, for preventing and/or treating pruritis and/or seborrhoeic dermatitis of the scalp, for re-establishing a balanced ecoflora of the scalp, for improving and/or re-establishing the antimicrobial defences of a dry or a greasy or an oily scalp, for improving the comfort of the skin and the scalp, for improving the hygiene and/or care of the scalp, for giving the scalp a feeling of well-being, for maintaining and/or restoring the biomechanical properties of the scalp, for preserving and/or reinforcing the integrity of the barrier functions of the skin of the scalp, for preventing and/or treating pruritus and/or seborrhoeic dermatitis associated with dandruff conditions of the scalp, and for preventing and/or treating the inflammations associated with dandruff conditions of the scalp.

Process

A process according to the invention includes at least two periods of time, which are consecutive to each other, together forming a sequence known as the "treatment sequence".

A process according to the invention includes at least a first treatment sequence, or even a succession of several sequences, for example at least two, three or four consecutive treatment sequences.

A treatment sequence may thus be repeated so as to obtain a succession of first and second periods of time.

Advantageously, a process of the invention includes a sequence repeated at least once, in particular at least twice and preferably at least three times.

Alternatively, the succession of the treatment sequences may include between each sequence a phase of stopping the treatments, ranging from a few days, for example 1, 2, 3, 4 or 5 days, to a few weeks, for example 1, 2, 3 or 4 weeks.

The first and second periods of time may range from a few days, for example 2, 3, 4, 5, 6 or 7 days, to a few weeks, for example 2, 3, 4, 5 or 6 weeks.

According to one embodiment, the two periods of time may range, independently of each other, from one week to six weeks, preferably from two to five weeks and preferentially from three to four weeks.

According to one embodiment, the first and second periods of time may be of different duration. For example, the first period of time may be shorter than the second, or, conversely, the second period of time may be shorter than the first.

According to another embodiment, the first period of time is equal to the second period of time.

The administration of the active agents is performed at least once per period of time. Preferably, the periods of time may be broken into units of time, in particular of equal duration, for example into days or weeks. In such an embodiment, the administration of the active agents is performed at least once per unit of time, for example at least once a day.

As indicated previously, the first cosmetic active agent is administered over the two periods of time, whereas the second cosmetic active agent is administered only over a single period of time chosen between the first and the second period of time.

Advantageously, the second cosmetic active agent may be administered over the first period of time.

Thus, according to one preferred embodiment of the invention, a process of the invention may include a first period of time including the administration of the first and second cosmetic active agents, the said first period of time being followed by a second period of time including the administration of the first cosmetic active agent in the absence of the second cosmetic active agent.

According to yet another embodiment, a process of the invention may include a first period of time including the administration of the first cosmetic active agent in the absence of the second cosmetic active agent, the said first period of time being followed by a second period of time including the administration of the first and second cosmetic active agents.

When the first cosmetic active agent is administered in the absence of the second cosmetic active agent over a period of time, it may be administered via any route known to those skilled in the art, especially orally or topically, and in particular orally.

Since the first and second cosmetic active agents are formulated in separate compositions, when they are administered over the same period of time, they may be administered via identical or different routes of administration. In particular, the second cosmetic active agent is administered topically, and the first cosmetic active agent may be administered orally or topically, and preferably orally.

When they are administered over the same period of time, the first and second cosmetic active agents may be administered sequentially over time, i.e. consecutively one after the other, separately, i.e. each at a given moment of the period of time, or concomitantly.

Within the same period of time, the first and second cosmetic active agents may be administered, without preference, in any order, for example the first active agent before the second, or the second before the first active agent.

During a concomitant administration, the topical administration of the second cosmetic active agent is preferably performed first so as to be in place during the oral administration of the first cosmetic active agent.

According to one preferred embodiment, the first period of time covers four weeks and includes the administration of the first and second active agents once a day, and the second period of time covers four weeks and includes the administration of the first active agent once a day, and stoppage of the second active agent.

Probiotic Microorganisms

For the purposes of the present invention, the term "probiotic microorganisms" means a live microorganism which, when consumed in adequate amount, has a positive effect on the health of its host ("*Joint FAO/WHO Expert Consultation on Evaluation of Health and Nutritional Properties of Probiotic in Food Including Powder Milk with Live Lactic Acid Bacteria,* 6 Oct. 2001"), and which may in particular improve the intestinal microbial balance.

According to one variant of the invention, a microorganism according to the invention may be used in an isolated form, i.e. not mixed with one or more compound(s) liable to be associated with it in its medium of origin.

For the purposes of the invention, the term "metabolite" denotes any substance derived from the metabolism of the microorganisms under consideration according to the invention and also having efficacy in the treatment of dandruff conditions of the scalp.

For the purposes of the invention, the term "fraction" more particularly denotes a fragment of the said microorganism, which has efficacy in the treatment of dandruff conditions of the scalp by analogy with the said whole microorganism.

According to one preferred embodiment, the probiotic microorganism metabolites and/or fractions that are suitable for use in the invention may be administered in the form of a lysate.

For the purposes of the invention, a "lysate" conventionally denotes a material obtained after the destruction or dissolution of biological cells via a phenomenon known as cell lysis, thus giving rise to the release of the intracellular biological constituents naturally contained in the cells of the microorganism under consideration.

For the purposes of the present invention, the term "lysate" is used without preference to denote the whole lysate obtained via lysis of the microorganism under consideration or only a fraction thereof.

The lysate used is thus totally or partially formed from the intracellular biological constituents and from the constituents of the cell walls and membranes.

Advantageously, a lysate used for the invention may be the whole lysate obtained via lysis of the microorganism under consideration.

This cell lysis may be accomplished via various techniques, such as an osmotic shock, a heat shock, via ultrasonication, or alternatively under a mechanical stress of centrifugation type.

More particularly, this cell lysate may be obtained according to the technique described in U.S. Pat. No. 4,464,362, and especially according to the following protocol.

In particular, a lysate of the invention may be obtained via ultrasonic disintegration of a medium comprising probiotic microorganisms in order to release therefrom the cytoplasmic fractions, the cell wall fragments and the products derived from metabolism. All the components in their natural distribution are then stabilized in a weakly acidic aqueous solution.

A lysate may be used in various forms, in the form of a solution or in a pulverulent form.

The microorganism(s) may be included in a composition according to the invention in live, semi-active or inactivated or dead form.

For the purposes of the invention, an "inactivated" or "dead" microorganism is a microorganism that is no longer capable of forming colonies in cultures. The dead or inactivated microorganisms may have intact or broken cell membranes. The dead or inactivated microorganisms may be obtained via any method known to those skilled in the art.

According to one embodiment, a probiotic microorganism that is suitable for a use and in particular for a process of the invention may be chosen from *Lactobacillus* sp., *Bifidobacterium* sp., *Cocci*, yeasts and sporulated bacteria, and mixtures thereof.

Preferably, a microorganism suitable for a use according to the invention is a probiotic microorganism, in particular of the *Lactobacillus* and/or *Bifodobacterium* sp. genus.

According to one embodiment, a microorganism that may be suitable for the invention, and in particular for a process of the invention, may be preferentially chosen from ascomycetes such as *Saccharomyces, Yarrowia, Kluyveromyces, Torulaspora, Schizosaccharomyces pombe, Debaromyces, Candida, Pichia, Aspergillus* and *Penicillium*, bacteria of the genus *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*, and mixtures thereof.

As ascomycetes most particularly suitable for the present invention, mention may in particular be made of *Yarrowia lipolitica* and *Kluyveromyces lactis*, and likewise *Saccharomyces cereviseae, Torulaspora, Schizosaccharomyces pombe, Candida* and *Pichia*.

According to one embodiment, a probiotic microorganism that is suitable for a use, and in particular in a process, of the invention may be chosen from:

lactic acid bacteria: which produce lactic acid by fermentation of sugar.

According to their morphology, they are divided up into two groups:

*Lactobacillus* species: *Lactobacillus acidophilus, amylovorus, casei, rhamnosus, brevis, crispatus, delbrueckii* (subsp *bulgaricus, lactis), fermentum, helveticus, gallinarum, gasseri, johnsonii, plantarum, reuteri, salivarius, alimentarius, curvatus, casei* subsp. *casei, sake,* and

*Cocci: Enterococcus (faecalis, faecium), Lactococcus lactis* (subsp *lactis* or *cremoris), Leuconostoc mesenteroides* subsp *dextranicum, Pediococcus acidilactici, Sporolactobacillus inulinus, Streptococcus salvarius* subsp. *thermophilus, Streptococcus thermophilus, Staphylococcus carnosus, Staphylococcus xylosus,* bifidobacteria or *Bifidobacterium* species: *Bifidobacterium adolescentis, animalis, bifidum, breve, lactis, longum, infantis, pseudocatenulatum,* yeasts: *Saccharomyces (cerevisiae* or *boulardii),* other sporulated bacteria: *Bacillus (cereus* var *toyo* or *subtilis), Bacillus coagulans, Bacillus licheniformis, Escherichia coli* strain *nissle, Propionibacterium freudenreichii,* and mixtures thereof.

As other examples of probiotic microorganisms that are suitable for the invention, mention may be made of *Bifidobacterium adolescentis, Bifidobacterium animalis, Bifidobacterium bifidum, Bifidobacterium breve, Bifidobacterium lactis, Bifidobacterium longum, Bifidobacterium infantis, Bifidobacterium pseudocatenulatum, Lactobacillus acidophilus* NCFB 1748; *Lactobacillus amylovorus, Lactobacillus casei (Shirota), Lactobacillus rhamnosus* strain GG, *Lactobacillus brevis, Lactobacillus crispatus, bulgaricus, Lactobacillus delbrueckii* subsp., *lactis, Lactobacillus fermentum, Lactobacillus helveticus, Lactobacillus gallinarum, Lactobacillus gasseri, Lactobacillus johnsonii* CNCM I-1225, *Lactobacillus plantarum, Lactobacillus reuteri, Lactobacillus salivarius, Lactobacillus alimentarius, Lactobacillus curvatus, Lactobacillus casei* subsp. *casei, Lactobacillus sake, Lactococcus lactis, Enterococcus faecalis, Enterococcus faecium, Lactococcus lactis* subsp. *lactis, Lactococcus lactis* subsp *cremoris, Leuconostoc mesenteroides* subsp. *dextranicum, Pediococcus acidilactici, Sporolactobacillus inulinus, Streptococcus salvarius* subsp. *thermophilus, Streptococcus thermophilus, Staphylococcus carnosus, Staphylococcus xylosus, Saccharomyces cerevisiae, Saccharomyces boulardii, Bacillus cereus* var. *toyo, Bacillus cereus* var. *subtilis, Bacillus coagulans, Bacillus licheniformis, Escherichia coli* strain nissle and *Propionibacterium freudenreichii*, and mixtures thereof.

More particularly, it may be a probiotic microorganism chosen from *Lactobacillus* sp., *Sporolactobacillus* sp., *Enterococcus* sp., *Lactococcus* sp., *Bacillus* sp., *Streptococcus* sp., *Pediococcus* sp., *Leuconostoc* sp. and *Bifidobacterium* sp., and in particular chosen from *Lactobacillus* sp. and *Bifidobacterium* sp., and mixtures thereof.

More particularly, a microorganism useful for the invention may be a probiotic microorganism chosen from *Lactobacillus* sp. and/or *Bifidobacterium* sp.

As illustrations of these probiotic microorganisms, mention may be made more particularly of *Lactobacillus johnsonii*, *Lactobacillus reuteri*, *Lactobacillus rhamnosus*, *Lactobacillus paracasei*, *Lactobacillus casei*, *Bifidobacterium bifidum*, *Bifidobacterium breve*, *Bifidobacterium longum*, *Bifidobacterium animalis*, *Bifidobacterium lactis*, *Bifidobacterium infantis*, *Bifidobacterium adolescentis* and *Bifidobacterium pseudocatenulatum*, and mixtures thereof.

The species most particularly suitable are *Lactobacillus johnsonii*, *Lactobacillus paracasei*, *Bifidobacterium adolescentis* and *Bifidobacterium longum*, respectively deposited according to the Treaty of Budapest with the Institut Pasteur (28 rue du Docteur Roux, F-75024 Paris cedex 15) on Jun. 30, 1992, Jan. 12, 1999, Apr. 15, 1999 and Apr. 15, 1999 under the following designations: CNCM I-1225, CNCM I-2116, CNCM I-2168 and CNCM I-2170, and the *Bifidobacterium lactis* (Bb 12) (ATCC27536) or *Bifidobacterium longum* (BB536) genus. The *Bifidobacterium lactis* (ATCC27536) strain can be obtained from Hansen (Chr. Hansen A/S, 10-12 Boege Alle, P.O. Box 407, DK-2970 Hoersholm, Denmark).

Advantageously, a microorganism that is suitable for use in the invention may be a lactic acid probiotic microorganism.

According to one preferred embodiment, a probiotic microorganism that is suitable for use in the invention may in particular be a microorganism of the genus *Lactobacillus* sp.

According to one particular embodiment of the invention, the microorganism is other than a *Lactobacillus rhamnosus*.

Preferably, a microorganism of the *Lactobacillus* sp. genus suitable for the invention may be chosen from the species *Lactobacillus johnsonii*, *Lactobacillus reuteri*, *Lactobacillus paracasei* and *Lactobacillus casei*, and mixtures thereof.

According to one preferred embodiment, a microorganism suitable for the invention may be a *Lactobacillus paracasei*.

A microorganism suitable for the invention may in particular be the *Lactobacillus paracasei* ST11 strain deposited according to the Treaty of Budapest with the Institut Pasteur (28 rue du Docteur Roux, F-75024 Paris cedex 15) on Jan. 12, 1999 under the designation CNCM I-2116, and/or a fraction thereof and/or a metabolite thereof.

According to another preferred embodiment, a probiotic microorganism that is suitable for use in the invention may in particular be a microorganism of the genus *Bifidobacterium* sp., and in particular *Bifidobacterium longum*, especially *Bifidobacterium longum* (BB536).

Advantageously, a *Bifidobacterium longum* may be used in the form of a lysate, obtained especially as described above.

A microorganism of the invention may be formulated in a composition in a proportion of at least 0.0001% expressed as dry weight, in particular in a proportion from 0.0001% to 20% and more particularly in a proportion from 0.001% to 15% by weight, in particular from 0.01% to 10% by weight and especially from 0.1% to 2% by weight relative to the total weight of the composition containing it.

In general, a composition according to the invention, and in particular that intended to be administered orally, may comprise, for living microorganisms, from $10^3$ to $10^{15}$ cfu/g, in particular from $10^5$ to $10^{15}$ cfu/g, and more particularly from $10^7$ to $10^{12}$ cfu/g of microorganisms per gram of carrier or support, or at equivalent doses calculated for inactive or dead microorganisms or for microorganism fractions or for metabolites produced.

In particular, in a composition administered orally, the corresponding microorganism and/or fraction and/or metabolite concentration may be adjusted so as to correspond to doses (expressed as microorganism equivalent) ranging from $5 \times 10^5$ to $10^{13}$ cfu/day and in particular from $10^8$ to $10^{11}$ cfu/day.

A composition for topical application according to the invention may generally comprise from $10^3$ to $10^{12}$ cfu/g, in particular from $10^5$ to $10^{10}$ cfu/g and more particularly from $10^7$ to $10^9$ cfu/g of microorganisms.

The microorganism(s) may be included in a composition according to the invention in a live, semi-active or inactivated, or dead form.

In the particular case of a topical administration, it may be advantageous to use microorganisms in inactivated or even dead form.

The microorganism(s) may also be included in the form of fractions of cell components or in the form of metabolites. The microorganism(s), metabolite(s) or fraction(s) may also be introduced in the form of a lyophilized powder, a culture supernatant and/or, where appropriate, in a concentrated form.

When a composition comprises metabolites, the contents of metabolites in the compositions correspond substantially to the contents that may be produced by $10^3$ to $10^{15}$ cfu, in particular $10^5$ to $10^{15}$ cfu and more particularly $10^7$ to $10^{12}$ cfu of live microorganisms per gram of support or carrier.

Expression of the amount of metabolites or fractions of a microorganism in "cfu", or of dead microorganisms, is intended to denote the amount of this microorganism that is necessary to produce the said amount of microorganism metabolites or fractions.

Cosmetic Active Agent

Additional Cosmetic Agent

According to one embodiment, a use of the invention, and in particular a process of the invention, implementing at least one probiotic microorganism in accordance with the invention, and in particular of the *Lactobacillus* sp. and/or *Bifidobacterium* sp., may be made in combination with an additional or a third cosmetic active agent.

Irrespective of the method of administration under consideration, the effective amount of the microorganism of the invention, a fraction thereof and/or a metabolite thereof, may also be advantageously combined with at least one other active agent.

More particularly, according to one embodiment, a process according to the invention may include, besides the administration of the first and second cosmetic active agents defined previously, the administration of at least a third or additional cosmetic active agent.

A third cosmetic active agent may be administered, without preference, over one or the other period of time defined previously, or even over both periods of time.

A third cosmetic active agent may be formulated together with the first and/or the second cosmetic active agent(s) defined previously, or may be formulated in a separate composition.

When the third or additional cosmetic active agent is formulated in a composition separate from the compositions comprising the first and second cosmetic active agents, it may be administered orally or topically. The route of administration is chosen by a person skilled in the art so as to be more particularly suited to the nature of the third cosmetic active agent.

Advantageously, such an additional or third cosmetic active agent may be intended for exerting a cosmetic, care or hygiene effect on the hair and/or the scalp, and in particular may be intended for reinforcing the skin barrier.

According to one embodiment, a third or additional cosmetic active agent suitable for a process of the invention may be chosen especially from a hair dyeing agent, an agent for preventing hair loss and/or for promoting hair regrowth, a detangler, a hair shaping agent, an agent for preventing and/or treating baldness, an anti-seborrhoea agent, an antibiotic, a hormone, an antiandrogen, an additional probiotic microorganism, in particular a lysate of *Bifidobacterium longum* or of *Vitreoscilla filiformis*, a hydrating agent, an antioxidant and a vitamin, and mixtures thereof.

Such a formulation may advantageously amplify the beneficial effects of a microorganism of the invention.

According to another embodiment, a topical or oral composition, or a combination according to the invention may contain at least one active agent chosen from an antiseborrhoeic active agent, a hydrating active agent, an antidandruff active agent as described below, and/or mixtures thereof.

An additional or third cosmetic active agent may be chosen from:

anti-seborrhoeic active agents. The term "antiseborrhoeic active agent" is intended to mean a compound capable of regulating sebaceous gland activity. The antiseborrhoeic active agent is, for example, present in a content ranging from 0.1% to 10% by weight, preferably from 0.1% to 5% by weight, and preferentially from 0.5% to 3% by weight, relative to the total weight of the composition.

As example of anti-seborrhoeic active agents one may mention certain sulfur-containing amino acids, 13-cis-retinoic acid, cyproterone acetate, benzoyl peroxide, sulphur, vitamin B6 (or pyridoxine), selenium chloride, sea fennel; mixtures of extract of cinnamon, of tea and of octanoylglycine, such as Sepicontrol A5 TEA® from Seppic; the mixture of cinnamon, sarcosine and octanoylglycine sold in particular by the company SEPPIC under the trade name Sepicontrol A5®; zinc salts such as zinc gluconate, zinc pyrrolidonecarboxylate (or zinc pidolate), zinc lactate, zinc aspartate, zinc carboxylate, zinc salicylate, zinc cysteate; copper derivatives, and in particular copper pidolate such as Cuivridone® from Solabia; extracts of plants of the species *Arnica montana, Cinchona succirubra, Eugenia caryophyllata, Humulus lupulus, Hypericum perforatum, Mentha piperita, Rosmarinus officinalis, Salvia officinalis* and *Thymus vulgaris*, all sold, for example, by the company Maruzen; extracts of meadowsweet (*Spiraea ulmaria*) such as the product sold under the name Sebonormine® by the company Silab; extracts of the alga *Laminaria saccharina* such as the product sold under the name Phlorogine® by the company Biotechmarine; mixtures of extracts of salad burnet root (*Sanguisorba officinalis/Poterium officinale*), of ginger rhizomes (*Zingiber officinalis*) and of cinnamon bark (*Cinnamomum cassia*), such as the product sold under the name Sebustop® by the company Solabia; linseed extracts, such as the product sold under the name Linumine® by the company Lucas Meyer; Phellodendron extracts, such as those sold under the name Phellodendron extract BG® by the company Maruzen or Oubaku liquid B by the company Ichimaru Pharcos; mixtures of argan oil, of *Serenoa serrulata* (saw palmetto) extract and of sesame seed extract, such as the product sold under the name Regu SEB® by the company Pentapharm; mixtures of extracts of willowherb, of *Terminalia chebula*, of nasturtium and of bioavailable zinc (microalgae), such as the product sold under the name Seborilys® by the company Green Tech; extracts of *Pygeum afrianum*, such as the product sold under the name *Pygeum afrianum* sterolic lipid Extract® by the company Euromed; extracts of *Serenoa serrulata*, such as those sold under the name Viapure Sabal® by the company Actives International, or those sold by the company Euromed; mixtures of extracts of plantain, of *Berberis aquifolium* and of sodium salicylate, such as the product sold under the name Seboclear® by the company Rahn; clove extract, such as the product sold under the name Clove extract Powder® by the company Maruzen; argan oil, such as the product sold under the name Lipofructyl® by Laboratoires Sérobiologiques; lactic protein filtrates, such as the product sold under the name Normaseb® by the company Sederma; extracts of the alga *Laminaria*, such as the product sold under the name Laminarghane® by the company Biotechmarine; oligosaccharides of the alga *Laminaria digitata*, such as the product sold under the name Phycosaccharide AC® by the company Codif; cane sugar extracts, such as the product sold under the name Policosanol® by the company Sabinsa; sulphonated shale oil, such as the product sold under the name Ichthyol Pale® by the company Ichthyol; extracts of European meadowsweet (*Spiraea ulmaria*), such as the product sold under the name Cytobiol® Ulmaire by the company Libiol; sebacic acid, in particular sold in the form of a sodium polyacrylate gel under the name Sebosoft® by the company Sederma; glucomannans extracted from konjac tuber and modified with alkylsulphonate chains, such as the product sold under the name Biopol Beta® by the company Arch Chemical; extracts of *Sophora angustifolia*, such as those sold under the name Sophora Powder® or Sophora Extract® by the company Bioland; extracts of *Cinchona succirubra* bark, such as the product sold under the name Red bark HS® by the company Alban Muller; extracts of *Quillaja saponaria*, such as the product sold under the name Panama wood HS® by the company Alban Muller; glycine grafted onto an undecylenic chain, such as the product sold under the name Lipacide UG OR® by the company Seppic; the mixture of oleanolic acid and of nordihydroguaiaretic acid, such as the product sold in the form of a gel under the name AC.Net® by the company Sederma; phthalimidoperoxyhexanoic acid; tri($C_{12}$-$C_{13}$) alkyl citrate sold under the name Cosmacol® ECI by the company Sasol; tri($C_{14}$-$C_{15}$)alkyl citrate sold under the name Cosmacol® ECL by the company Sasol; 10-hydroxydecanoic acid, and in particular mixtures of 10-hydroxydecanoic acid, of sebacic acid and of 1,10-decanediol, such as the product sold under the name Acnacidol® BG by the company Vincience; and mixtures thereof, agents for preventing hair loss and/or for promoting hair regrowth such as nicotinic acid esters, especially including tocopheryl nicotinate, benzyl nicotinate and $C_1$-$C_6$ alkyl nicotinates, for instance methyl or hexyl nicotinate; pyrimidine derivatives such as 2,4-diamino-6-piperidinopyrimidine 3-oxide or Minoxidil described in U.S. Pat. No. 4,139,619 and U.S. Pat. No. 4,596,812; Aminexil or 2,4-diaminopyrimidine 3-oxide, described in WO 96/09048; agents that are both lipoxygenase inhibitors and cyclooxygenase inducers, or cyclooxygenase inducers that promote hair regrowth such as those described in European patent application EP 0 648 488;

antibiotics such as macrolides, pyranosides and tetracyclines, and especially erythromycin;

hormones such as oestriol or analogues thereof, thyroxine and salts thereof;

antiandrogens such as oxendolone, spironolactone, diethylstilbestrol and flutamide hair dyeing agents;

detanglers;

hair shaping agents;

agents for preventing and/or treating baldness;

antidandruff agents as detailed below, hydrating active agent. An hydrating active agent is an active agent capable of reducing the state of dryness of an epidermis.

The term "hydrating active agent" is intended to mean:
either a compound which acts on the barrier function, with a view to maintaining the hydration of the stratum corneum, or an occlusive compound. Mention may be made of ceramides, sphingoid-based compounds, lecithins, glycosphingolipids, phospholipids, cholesterol and its derivatives, phytosterols (stigmasterol, β-sitosterol, campesterol), essential fatty acids, 1,2-diacylglycerol, 4-chromanone, pentacyclic triterpenes, petroleum jelly and lanolin;

or a compound which directly increases the water content of the stratum corneum, such as urea and its derivatives, threalose and its derivatives, hyaluronic acid and its derivatives, glycerol, pentanediol, pidolates, serine, xylitol, lactic acid and sodium lactate, glyceryl polyacrylate, ectoin and its derivatives, chitosan, oligosaccharides and polysaccharides, cyclic carbonates, N-lauroylpyrrolidonecarboxylic acid and N-α-benzoyl-L-arginine;

or a compound which activates the sebaceous glands, such as steroidal derivatives (including DHEA), and vitamin D and its derivatives.

These compounds may represent from 0.001% to 3%, and preferably from 0.01% to 20%, of the total weight of the composition according to the invention.

By way of illustration of the urea derivatives, mention may more particularly be made of hydroxyalkylurea derivatives, and in particular those described in document FR 2 877 222.

According to one embodiment variant, a third or additional cosmetic active agent useful in a process of the invention may be a microorganism referred to as a "second microorganism", especially of probiotic type, and/or a fraction thereof, and/or a metabolite thereof, which is different from the said first microorganism defined as first cosmetic active agent.

According to one variant embodiment, the invention relates to the use, in addition of a first probiotic microorganism, for example as defined above, of the *Lactobacillus* and/or *Bifidobacterium* sp. genus, of at least an effective amount of at least a second microorganism, in particular of probiotic type, and/or a fraction thereof and/or a metabolite thereof, distinct from said first microorganism.

For the purposes of the invention, as previously exposed the expression "different from the said first probiotic microorganism" means that it is possible to distinguish within the same composition either two different microorganisms, or two different forms of the same microorganism. Thus, when the second microorganism is, for example, of the genus *Lactobacillus* sp. or *Bifidobacterium* sp. and corresponds to the same species as that of the invention, this second microorganism is then present in a form different from the first microorganism.

The second probiotic microorganism may be formulated in the same composition as that containing the first cosmetic active agent, or in the same composition as that containing the second cosmetic active agent, or alternatively may be formulated in a third composition separate from the above-mentioned compositions.

More particularly, it may be one of the probiotic microorganisms proposed hereinabove, as a specific example of probiotic microorganisms for the first cosmetic active agent or as "second microorganism".

This second microorganism may be chosen in particular from ascomycetes such as *Saccharomyces, Yarrowia, Kluyveromyces, Torulaspora, Schizosaccharomyces pombe, Debaromyces, Candida, Pichia, Aspergillus* and *Penicillium*, bacteria of the *Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus, Lactobacillus* or *Bifidobacterium* genus, and mixtures thereof.

According to one embodiment, the following bacterial and yeast genera are preferentially used as second microorganism:

lactic acid bacteria:

*Lactobacillus* species: *Lactobacillus acidophilus, amylovorus, casei, rhamnosus, brevis, crispatus, delbrueckii* (subsp *bulgaricus, lactis*), *fermentum, helveticus, gallinarum, gasseri, johnsonii, plantarum, reuteri, salivarius, alimentarius, curvatus, casei* subsp. *casei, sake*, and Cocci: *Enterococcus (faecalis, faecium), Lactococcus lactis* (subsp *lactis* or *cremoris*), *Leuconostoc mesenteroides* subsp *dextranicum, Pediococcus acidilactici, Sporolactobacillus inulinus, Streptococcus salvarius* subsp. *thermophilus, Streptococcus thermophilus, Staphylococcus carnosus, Staphylococcus xylosus,* bifidobacteria or *Bifidobacterium* species: *Bifidobacterium adolescentis, animalis, bifidum, breve, lactis, longum, infantis, pseudocatenulatum,* yeasts: *Saccharomyces (cerevisiae* or *boulardii),* other sporulated bacteria: *Bacillus (cereus* var *toyo* or *subtilis), Bacillus coagulans, Bacillus licheniformis, Escherichia coli* strain *nissle, Propionibacterium freudenreichii,* and mixtures thereof.

More particularly, the second microorganism may be one of the probiotic microorganisms proposed above, by way of specific example of probiotic microorganisms for the first organism.

According to one particular embodiment, the third or additional cosmetic active agent is a second probiotic microorganism of the genus *Lactobacillus* sp., in particular *Lactobacillus johnsonii*, a fraction thereof and/or a metabolite thereof.

The species most particularly suitable are *Lactobacillus johnsonii, Bifidobacterium adolescentis, Bifidobacterium longum* and *Bifidobacterium lactis* NCC 2818, respectively deposited according to the Treaty of Budapest with the Institut Pasteur (28 rue du Docteur Roux, F-75024 Paris cedex 15) on Jun. 30, 1992, Jan. 12, 1999, Apr. 15, 1999, Apr. 15, 1999 and Jun. 7, 2005 under the following designations: CNCM I-1225, CNCM I-2168, CNCM I-2170 and CNCM I-3446, and the *Bifidobacterium longum* (BB536) genus, and mixtures thereof.

According to one particular embodiment, the second probiotic microorganism is of the *Lactobacillus* species genus, in particular of the species *Lactobacillus johnsonii*, a fraction thereof and/or a metabolite thereof.

It may in particular be the species *Lactobacillus johnsonii* respectively deposited according to the Treaty of Budapest with the Institut Pasteur (28 rue du Docteur Roux, F75024 Paris cedex 15) on Jun. 30, 1992, under the designation CNCM I-1225.

According to another particular embodiment, the third or additional cosmetic active agent is a second probiotic microorganism of the genus *Bifidobacterium* sp., and in particular *Bifidobacterium longum*, especially *Bifidobacterium longum* (BB536).

According to one embodiment, when the third or additional cosmetic active agent is a second probiotic microorganism, it may advantageously be used in the form of a lysate, especially obtained as described above. In particular, the second probiotic microorganism may be a lysate of *Bifidobacterium longum*.

According to yet another embodiment, a third or additional cosmetic active agent which may be an additional microorganism suitable for use in the invention may be chosen from non-photosynthetic filamentous bacteria and/or a fraction thereof and/or a metabolite thereof. These bacteria may also be advantageously formulated in lysate form.

As illustrations of these bacteria, mention may be made especially of the non-photosynthetic filamentous bacteria as defined according to the classification in Bergey's Manual of Systematic Bacteriology (Vol. 3, sections 22 and 23, 9th edition, 1989), among which mention may be made of the bacteria belonging to the order of Beggiatoales, and more particularly the bacteria belonging to the genus *Beggiatoa, Vitreoscilla, Flexithrix* or *Leucothrix*.

Among the bacteria that may be used, mention may be made, for example, of *Vitreoscilla filiformis* (ATCC 15551), *Vitreoscilla beggiatoides* (ATTC 43181), *Beggiatoa alba* (ATCC 33555), *Flexithrix dorotheae* (ATCC 23163), *Leucothrix mucor* (ATCC 25107) and *Sphaerotilus natans* (ATCC 13338).

According to an embodiment of invention an additional or third active agent, for example contained in topical or oral compositions, or combinations of the invention may be an active agent in particular intended to reinforce the cutaneous barrier.

By way of additional or third active agents that can be used, mention may be made of vitamins, such as vitamin A, B3, B5, B6, B8, C, D, E or PP; antioxidants, such as curcuminoids, carotenoids, polyphenol; inorganic (or minerals) compounds; sugars; amino acids; sulfur-containing amino acids; 3 and 6 polyunsaturated fatty acids; taurine and phytosterols.

In particular, use may be made of an antioxidant complex comprising vitamins C and E, and at least one carotenoid, especially a carotenoid chosen from β-carotene, lycopene, astaxanthin, zeaxanthin and lutein, flavonoids such as catechins, proanthocyanidins, anthocyanins, ubiquinones, coffee extracts containing polyphenols and/or diterpenes, extracts of chicory, extracts of *ginkgo biloba*, proanthocyanidin-rich grape extracts, extracts of *capsicum*, soya bean extracts, other sources of flavonoids having antioxidant properties, fatty acids, prebiotics, taurine, resveratrol, selenium-containing amino acids and glutathione precursors.

Among the flavonoids, catechins and OPCs (oligomeric proanthocyanidins) are preferably chosen.

At least one prebiotic or a mixture of prebiotics may also be involved. More particularly, these prebiotics may be chosen from oligosaccharides, produced from glucose, galactose, xylose, maltose, sucrose, lactose, starch, xylan, hemicellulose or inulin, gums of acacia type for example, or a mixture thereof. More particularly, the oligosaccharide comprises at least one fructooligosaccharide. More particularly, this prebiotic may comprise a mixture of fructooligosaccharide and inulin.

In the topical galenic forms, use may more particularly be made, as hydrophilic active agents, of proteins or protein hydrolysates, amino acids, polyols, in particular $C_2$ to $C_{10}$ polyols such as glycerol, sorbitol, butylene glycol and polyethylene glycol, urea, allantoin, sugars and sugar derivatives, water-soluble vitamins, starch, and bacterial extracts or plant extracts such as those of Aloe Vera.

As regards the lipophilic active agents, use may be made of retinol (vitamin A) and derivatives, tocopherol (vitamin E) and derivatives, ceramides, essential oils and unsaponifiable materials (tocotrienol, sesamine, gamma-oryzanol, phytosterols, squalenes, waxes and terpenes).

As additional or third active agents that may also be combined with the microorganism of the invention, with a fraction thereof and/or with a metabolite thereof, in an oral galenical formulation, any ingredient commonly used and/or permitted may also be considered.

By way of illustration, mention may be made of vitamins, minerals, essential lipids, trace elements, polyphenols, flavonoids, phytoestrogens, antioxidants such as lipoic acid and coenzyme Q10, carotenoids, prebiotics, proteins and amino acids, monosaccharides and polysaccharides, amino sugars, phytosterols and triterpenic alcohols of plant origin.

This may involve, in particular of vitamins A, C, D, E, PP and group B vitamins. Among the carotenoids, beta-carotene, lycopene, lutein, zeaxanthin and astaxanthin are preferably chosen. The minerals and trace elements particularly used are zinc, calcium, magnesium, copper, iron, iodine, manganese, selenium and chromium (III).

Among the polyphenol compounds, polyphenols from grape, from tea, from olive, from cocoa, from coffee, from apple, from blueberry, from elderberry, from strawberry, from cranberry and from onion are also in particular selected. Preferably, among the phytoestrogens, isoflavones in free or glycosylated form are selected, such as genistein, daidzein, glycitein or alternatively lignans, in particular those from flax and from *Schizandra chinensis*.

The amino acids or the peptides and the proteins containing them, such as taurine, threonine, cysteine, tryptophan or methionine. The lipids preferably belong to the group of oils containing monounsaturated and polyunsaturated fatty acids such as oleic acid, linoleic acid, alpha-linolenic acid, gamma-linolenic acid, stearidonic acid, long-chain fish omega-3 fatty acids such as EPA and DHA, and conjugated fatty acids derived from plants or animals, such as CLAs (Conjugated Linoleic Acids).

Thus, in particular a microorganism of the invention, a fraction thereof and/or a metabolite thereof, orally administered may also be combined with at least one nutritional active agent chosen from lycopene, vitamin C, vitamin E and polyphenol compounds.

An oral composition of the invention may comprise other nutritional active agents chosen from:
  anti-aging nutritional active agents, such as food antioxidants, nutrients with free-radical-scavenging properties and cofactors of antioxidant endogenous enzymes, vitamins A, C and E, carotenoids, xanthophylls, isoflavones, certain minerals such as zinc, copper, magnesium, selenium, lipoic acid, coenzyme Q10, superoxide dismutase (SOD) or taurine. Among the anti-aging active agents, mention may in particular be made of the unsaponifiable fractions extracted from lipids of plant origin, Aloe Vera, native or hydrolysed marine collagen, plant or marine oils rich in omega-3 and omega-6 fatty acids (including gamma-linolenic acid),
  photoprotective nutritional active agents such as: antioxidants and free-radical scavengers, vitamins A, C and E, carotenoids, xanthophylls, certain minerals such as zinc, copper, magnesium or selenium, coenzyme Q10, superoxide dismutase (SOD),
  nutritional ingredients with hydrating or else immunomodulatory properties, such as extract of *Polypodium leucotomos*, and plant or marine oils rich in omega-3 and omega-6 fatty acids, including gamma-linolenic acid.

Antidandruff Active Agents

A process according to the invention comprises a use of an antidandruff agent.

According to another embodiment, a use of at least one probiotic microorganism in accordance with the invention, and in particular of the *Lactobacillus* sp. and/or *Bifidobacterium* sp., may also comprise the use of an antidandruff agent.

The term "antidandruff active agent" is intended to mean a compound capable of preventing the appearance of dandruff, decreasing the amount thereof and/or making it completely disappear.

An antidandruff active agent that is suitable for use in the invention may be chosen especially from:

pyridinethione salts, especially the calcium, magnesium, barium, strontium, zinc, cadmium, tin and zirconium salts. The zinc salt of pyridinethione is particularly preferred. The zinc salt of pyridinethione is sold especially under the name Zinc Omadine by the company OLIN;

trihalocarbamides of formula:

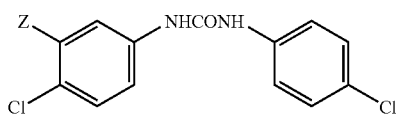

in which Z represents a halogen atom such as chlorine or a $C_1$-$C_4$ trihaloalkyl group such as $CF_3$;

triclosan, represented by the formula:

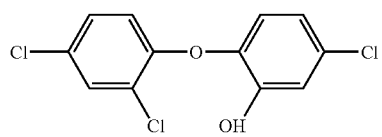 [SMILES: Oc1cc(Cl)ccc1Oc1ccc(Cl)cc1Cl]

azole compounds such as climbazole, ketoconazole, clotrimazole, econazole, isoconazole and miconazole,
antifungal polymers such as amphotericin B or nystatin,
selenium sulfides, in particular those of formula $S_xSe_{8-x}$, x ranging from 1 to 7,
sulfur in its various forms, such as cadmium sulfide,
allantoin,
coal or wood tars and derivatives thereof, in particular cade oil,
salicylic acid,
undecylenic acid,
fumaric acid,
allylamines, such as terbinafine,
ciclopirox or octopirox,
piroctone olamine,
clobetasol propionate or betamethasone valerate,
tea tree oil,
mixed oil of thyme and of catnip,
an antidandruff probiotic or non-probiotic microorganism, especially a probiotic microorganism as defined previously as first cosmetic active agent or, as also previously defined, as third or additional cosmetic active agent. In particular, a probiotic microorganism that is suitable for use as antidandruff active agent may be a microorganism chosen from *Lactobacillus paracasei*, *Bifidobacterium longum* and *Vitreoscilla filiformis*, especially formulated in the form of a lysate as indicated hereinabove,
and mixtures thereof.

Preferentially examples of antidandruff agents that may especially be mentioned include zinc pyridinethione, salicylic acid, selenium disulfide, mixed oil of thyme and of catnip, octopirox or a probiotic microorganism, and mixtures thereof.

By way of preferred examples of antidandruff agents, mention may in particular be made of zinc pyrithione, salicylic acid and selenium disulphide, and mixtures thereof.

A composition according to the invention advantageously comprises from 0.001% to 10% by weight, preferably from 0.1% to 5% by weight and even more preferentially from 0.2% to 2% by weight of antidandruff agent(s) relative to the total weight of the composition.

Compositions and Assembly

An assembly in accordance with the invention comprises at least a first and a second cosmetic compositions, the first composition comprising at least an effective amount of at least a first cosmetic active agent, the said first cosmetic active agent being *Lactobacillus paracasei*, a fraction thereof and/or a metabolite thereof, and the second composition comprising at least an effective amount of at least a second cosmetic active agent chosen from antidandruff active agents and being administered topically.

According to one embodiment, an assembly in accordance with the invention may also comprise at least a third composition comprising at least an effective amount of at least a third cosmetic active agent, especially as defined previously.

Such a third composition may be administered orally or topically.

The compositions that are suitable for the invention may be in any galenical form normally available for the selected mode of administration.

The support or carrier may be of various nature, depending on the type of composition under consideration.

As regards more particularly the compositions for external topical administration, they may be aqueous, aqueous-alcoholic or oily solutions, solutions or dispersions of the lotion or serum type, emulsions of liquid or semi-liquid consistency, of the milk type, obtained by dispersion of a fatty phase in an aqueous phase (O/W) or vice-versa (W/O), or suspensions or emulsions of soft, semi-solid or solid consistency, of the cream type, aqueous or anhydrous gels, microemulsions, microcapsules, microparticles, or vesicular dispersions of ionic and/or non-ionic type.

These compositions are prepared according to the usual methods.

These compositions may in particular constitute cleansing, protective, treatment or care creams, skincare lotions, gels or foams, such as cleansing or disinfecting lotions, bath compositions or deodorant compositions.

The compositions according to the invention may also consist of solid preparations constituting cleansing soaps or bars.

They may also be used for the scalp in the form of solutions, creams, gels, emulsions or mousses, or alternatively in the form of aerosol compositions also containing a propellant under pressure.

A topical composition according to the invention, especially a second composition, may advantageously be formulated in any galenical form that is suitable for haircare, especially in the form of a hair lotion, a shampoo, especially an antidandruff shampoo, a hair conditioner, a detangler, a hair cream or gel, a styling lacquer, a hairsetting lotion, a treating lotion, a dye composition (especially for oxidation dyeing) optionally in the form of a colouring shampoo, a hair-restructuring lotion, a permanent-waving composition, a lotion or gel for combating hair loss, an antiparasitic shampoo or a medicated shampoo, especially an anti-seborrhoea shampoo, a scalp care product, which is especially anti-irritant, anti-ageing or restructuring, or which activates the blood circulation.

When the composition of the invention is an emulsion, the proportion of the fatty phase may range from 5% to 80% by weight, and preferably from 10% to 50% by weight, relative to the total weight of the composition. The oils, the emulsifiers and the coemulsifiers used in the composition in emulsion form are chosen from those conventionally used in the cosmetics and/or dermatological field. The emulsifier and the coemulsifier may be present, in the composition, in a proportion ranging from 0.3% to 30% by weight, and preferably from 0.5% to 20% by weight, relative to the total weight of the composition.

When the composition of the invention is an oily gel or solution, the fatty phase may represent more than 90% of the total weight of the composition.

In a known manner, the galenic forms for topical administration may also contain adjuvants that are customary in the cosmetics, pharmaceutical and/or dermatological field, such as hydrophilic or lipophilic gelling agents, hydrophilic or lipophilic active agents, preservatives, antioxidants, solvents, fragrances, fillers, screens, odour absorbers and dyestuffs. The amounts of these various adjuvants are those conventionally used in the field under consideration, and are, for example, from 0.01% to 20% of the total weight of the composition. Depending on their nature, these adjuvants may be introduced into the fatty phase and/or into the aqueous phase.

As fatty substances that may be used in the invention, mention may be made of mineral oils such as, for example, hydrogenated polyisobutene and liquid petroleum jelly, plant oils such as, for example, a liquid fraction of shea butter, sunflower oil and apricot kernel oil, animal oils such as, for example, perhydrosqualene, synthetic oils, in particular Purcellin oil, isopropyl myristate and ethylhexyl palmitate, unsaturated fatty acids and fluoro oils such as, for example, perfluoropolyethers. Use may also be made of fatty alcohols, fatty acids such as, for example, stearic acid and such as, for example, waxes, in particular paraffin wax, carnauba wax and beeswax. Use may also be made of silicone compounds such as silicone oils and, for example, cyclomethicone and dimethicone, and silicone waxes, resins and gums.

As emulsifiers that may be used in the invention, mention may, for example, be made of glyceryl stearate, polysorbate 60, the mixture of cetylstearyl alcohol/oxyethylenated cetylstearyl alcohol comprising 33 mol of ethylene oxide, sold under the name Sinnowax AO® by the company Henkel, the mixture of PEG-6/PEG-32/glycol stearate sold under the name Tefose® 63 by the company Gattefosse, PPG-3 myristyl ether, silicone emulsifiers such as cetyl dimethicone copolyol and sorbitan monostearate or tristearate, PEG-40 stearate, or oxyethylenated sorbitan monostearate (20 EO).

As solvents that may be used in the invention, mention may be made of lower alcohols, especially ethanol and isopropanol, and propylene glycol.

The composition of the invention may also advantageously contain a spring and/or mineral water, in particular chosen from Vittel water, waters from the Vichy basin, and la Roche Posay water.

As hydrophilic gelling agents, mention may be made of carboxylic polymers such as carbomer, acrylic copolymers such as acrylate/alkyl acrylate copolymers, polyacrylamides, and in particular the mixture of polyacrylamide, C13-14 isoparaffin and Laureth-7 sold under the name Sepigel 305® by the company SEPPIC, polysaccharides, for instance derivatives such as hydroxyalkylcelluloses, and in particular hydroxypropylcellulose and hydroxyethylcellulose, natural gums such as guar gum, locust bean gum, carob and xanthan gum, and clays.

As lipophilic gelling agents, mention may be made of modified clays such as bentones, metal salts of fatty acids, such as aluminium stearates and hydrophobic silica, or else ethylcellulose and polyethylene.

In the case of oral use in accordance with the invention for oral administration, the use of an ingestible support or carrier is preferred.

The ingestible support or carrier may be of diverse nature depending on the type of composition under consideration.

Tablets or lozenges, oral supplements in dry form and oral supplements in liquid form are thus in particular suitable for use as dietetic or pharmaceutical supports or food carriers.

They may be, for example, food supplements, the formulation of which may be formulated via the usual processes for in particular producing sugar-coated tablets, gel capsules, gels, emulsions, tablets, capsules and hydrogels allowing controlled release.

In particular, a microorganism according to the invention may be incorporated into any other form of food supplement or enriched food, for example food bars or compacted or non-compacted powders. The powders may be diluted in water, soda, milk products or soya bean derivatives, or may be incorporated into food bars.

A microorganism of the invention, a fraction thereof and/or a metabolite thereof, may moreover be formulated with the usual excipients and components for such oral compositions or food supplements, i.e. in particular fatty and/or aqueous components, humectants, thickeners, preservatives, texturing agents, flavour enhancers and/or coating agents, antioxidants, preservatives and dyes that are customary in the food sector.

The formulating agents and excipients for oral compositions, and in particular for food supplements, are known in this field and will not be the subject of a detailed description herein.

Milk, yogurt, cheese, fermented milks, milk-based fermented products, ice creams, cereal-based products or fermented cereal-based products, milk-based powders, infant and baby formulas, food products of confectionary, chocolate or cereal type, animal feed, in particular for domestic animals, tablets, gel capsules or lozenges, liquid bacterial suspensions, oral supplements in dry form and oral supplements in liquid form are especially suitable for use as dietetic or pharmaceutical supports.

According to one embodiment, a composition according to the invention administered orally, especially a first composition, may be formulated in the form of coated tablets, gel capsules, gels, emulsions, tablets, capsules, hydrogels, food bars, compact or loose powders, liquid suspensions or solutions, confectionery products, fermented milks, fermented cheeses, chewing gum, toothpaste or spray solutions or food carriers.

In the description and in the examples that follow, unless otherwise indicated, the percentages are percentages by weight and the ranges of values written in the form "between . . . and . . . " include the upper and lower limits specified.

The ingredients are mixed, before being formulated, in the order and under conditions that can be readily determined by those skilled in the art.

The content and the nature of the ingredients used in the compositions of the invention are adjusted by those skilled in the art in such a way as not to substantially affect the properties required for the compositions of the invention.

EXAMPLES

Example 1

Powder Stick

| Active ingredient | |
|---|---|
| Lactobacillus paracasei ST11 | $10^{10}$ cfu |
| Excipient | |
| Xanthan gum | 0.8 mg |
| Sodium benzoate | 0.2 mg |
| Maltodextrin | qs 30 g |

One stick per day may be taken.

Example 2

Powder Stick

| Active ingredient | |
|---|---|
| Lactobacillus paracasei ST11 | $10^{10}$ cfu |
| Excipient | |
| Xanthan gum | 0.8 mg |
| Sodium benzoate | 0.2 mg |
| Maltodextrin | qs 30 g |

One stick per day may be taken.

Example 3

Formulation of Sugar-Coated Tablet Type

| Active materials | mg/sugar- |
|---|---|
| Lactobacillus paracasei ST11 | $5 \times 10^8$ cfu |
| Excipient of the sugar-coated | |
| Microcrystalline cellulose | 70 |
| Encompress ™ | 60 |
| Magnesium stearate | 3 |
| Anhydrous colloidal silica | 1 |
| Coating agent | |
| Shellac | 5 |
| Talc | 61 |
| Saccharose | 250 |
| Polyvidone | 6 |
| Titanium dioxide | 0.3 |
| Colouring agent | 5 |

This type of sugar-coated tablet can be taken 1 to 3 times a day.

Example 4

Formulation of Sugar-Coated Tablet Type

| Active materials | mg/sugar- |
|---|---|
| Lactobacillus paracasei ST11 | $10^9$ cfu |
| Lactobacillus johnsonii | $10^9$ cfu |
| Excipient of the sugar-coated | |
| Microcrystalline cellulose | 70 |
| Encompress ™ | 60 |
| Magnesium stearate | 3 |
| Anhydrous colloidal silica | 1 |
| Coating agent | |
| Shellac | 5 |
| Talc | 61 |
| Saccharose | 250 |
| Polyvinylidone | 6 |
| Titanium dioxide | 0.3 |
| Colouring agent | 5 |

This type of sugar-coated tablet can be taken 1 to 3 times a day.

Example 5

| Scalp lotion | |
|---|---|
| | % by weight |
| Lactobacillus paracasei ST11 powder | 5.00 |
| Lactobacillus johnsonii powder | 5.00 |
| Antioxidant | 0.05 |
| Isopropanol | 40.0 |
| Preservative | 0.30 |
| Water | qs 100 |

Example 6

| Scalp care milk | |
|---|---|
| | % by weight |
| Lactobacillus paracasei ST11 powder | 5.00 |
| Glyceryl stearate | 1.00 |
| Oil of cetylstearyl alcohol/oxyethylenated cetylstearyl alcohol comprising 30 mol EO (Sinnowax AO ® sold by the company Henkel) | 3.00 |
| Cetyl alcohol | 1.00 |
| Dimethicone (DC 200 Fluid ® sold by the company Dow Corning) | 1.00 |
| Liquid petroleum jelly | 6.00 |
| Isopropyl myristate (Estol IMP 1514 ® sold by Unichema) | 3.00 |
| Antioxidant | 0.05 |
| Glycerol | 20.00 |
| Preservative | 0.30 |
| Water | qs 100 |

Example 7

| Scalp care gel | |
|---|---|
| | % by weight |
| *Lactobacillus paracasei* ST11 powder | 5.00 |
| Hydroxypropylcellulose (Klucel H ® sold by the company Hercules) | 5.00 |
| Vitamin E | 1.00 |
| Antioxidant | 2.50 |
| Isopropanol | 0.05 |
| Preservative | 40.00 |
| Water | 0.30 |
| | qs 100 |

*Note: Vitamin E 2.50, Antioxidant 0.05, Isopropanol 40.00, Preservative 0.30*

Example 8

| Scalp care milk | |
|---|---|
| | % by weight |
| *Lactobacillus paracasei* ST11 powder | 5.00 |
| Glyceryl stearate | 1.00 |
| Cetylstearyl alcohol/oxyethylenated cetylstearyl alcohol comprising 3 mol EO (Sinnowax AO ® sold by the company Henkel) | 3.00 |
| Cetyl alcohol | 1.00 |
| Dimethicone (DC 200 Fluid ® sold by the company Dow Corning) | 1.00 |
| Liquid petroleum jelly | 6.00 |
| Isopropyl myristate (Estol IPM 1514 ® sold by the company Unichema) | 3.00 |
| Glycerol | 20.00 |
| Preservative | 0.30 |
| Water | qs 100 |

Example 9

| Scalp care cream | |
|---|---|
| | % by weight |
| Arachidyl behenyl alcohol/arachidylglucoside | 3.0 |
| Isohexadecane | 7.0 |
| *Lactobacillus paracasei* ST11 powder | 5.00 |
| Glycerol | 2.0 |
| Extract of *Vitreoscilla filiformis* | 3.0 |
| BHT | 0.05 |
| Methyl POB | 0.1 |
| Propyl POB | 0.05 |
| Water | qs 100 |

Example 10

| Hair care gel | |
|---|---|
| | % by weight |
| *Lactobacillus paracasei* ST11 powder | 5.00 |
| Copper citrate | 2.00 |
| Extract of *Vitreoscilla filiformis* | 3.00 |
| Antioxidant | 0.05 |
| Vitamin C | 2.50 |
| Antioxidant | 0.05 |
| Isopropanol | 40.00 |
| Preservative | 0.30 |
| Water | qs 100 |

Example 11

Effectiveness Study

Protocol

An oral composition based on probiotic microorganism (B) was tested for its effectiveness with respect to the dandruff condition and seborrhoeic dermatitis of the scalp, from the viewpoint of a placebo composition (A). The compositions are of the following formulation:

A: Maltodextrin

B: $1 \times 10^9$ cfu/g *Lactobacillus paracasei* ST11 NCC 2461 (CNCM I-2116).

The treatment comprises daily oral administration of a single amount of treatment for a period of eight weeks (56 days).

This study was carried out on 66 adult male individuals between 18 and 60 years old, and who were identified subsequent to a clinical evaluation of their dandruff condition, classified from moderate to severe, with scores greater than or equal to 3 (on a scale of 0 to 4) in the presence of adherent scales on at least two quarters of the head.

In the clinical evaluation, the presence of erythema and of seborrhoeic dermatitis of the scalp were also taken into consideration.

The 66 individuals were divided up into two parallel groups of 33 individuals, with one group receiving the tested product and one group receiving the placebo.

The effect of the supplement tested is assessed by comparison with the placebo formulation at D1, D15, D29, D43, D57 and D64 (after the treatment had been interrupted for one week), through clinical evaluations and self-evaluations carried out according to the following parameters: loose dandruff, adherent scales, erythema and seborrhoea of the scalp, facial seborrhoea and pruritis.

The clinical parameters evaluated are the presence of loose and adherent dandruff, the presence of scales, erythema, facial seborrhoea and seborrhoea of the scalp, and also measurement of the presence of *Malassezia* sp. yeast.

These evaluations are performed according to the usual techniques implemented in the field.

The parameters self-evaluated by the individuals treated are the presence of dandruff, pruritis, the feeling of an oily condition, irritations, redness, the feeling of tautness and the perception of the scalp, and also facial seborrhoea and seborrhoea of the hair.

The results obtained show a noticeable improvement, from the first weeks of treatment onwards, in the dandruff condition, in the erythema and in the seborrhoeic dermatitis of the scalp in the individuals treated with the composition B, compared with the individuals taking the placebo.

These evaluations were completed by counting the yeast of the *Malassezia* sp. genus on the scalp.

Results

A=Placebo (maltodextrin)

B=*Lactobacillus paracasei*, NCC 2461 (ST11) $10^9$ cfu/d

1. Clinical Evaluation:

a. Loose Dandruff

The results illustrated by FIG. 1 show a decrease in loose dandruff versus placebo, as a tendency from D15 ($p=0.057$), significant at D29 and up to D57 ($p<0.0001$).

The change between D1 and D57 is significant in favour of the active agent ($p=0.0005$). One week after interruption of the treatment, at D64, the effectiveness is maintained versus placebo between D1 and D64 ($p=0.0489$).

b. Adherent Dandruff

The results illustrated by FIG. 2 show a significant decrease in adherent dandruff versus placebo from D29 and up to D57 ($p<0.0001$).

The change between D1 and D57 is significant in favour of the active agent ($p=0.0005$).

c. Erythema

The results illustrated by FIG. 3 show a significant decrease in erythema versus placebo from D29 and up to D57 ($p=0.0015$).

The change between D1 and D57 is significant in favour of the active agent ($p=0.00469$). It is observed that the effectiveness of the composition of the invention is completely maintained between D57 and D64, from the viewpoint of this clinical aspect.

2. Self-Evaluations:

The results obtained by self-evaluation show profiles of the same type as those observed by clinical evaluation for the various parameters studied.

In particular, the effectiveness of the active agent with respect to pruritis is observed with a significant effect between D1 and D57 versus placebo ($p=0.0427$).

Likewise, the volunteers judged the decrease in the oily condition of their scalp to be very substantial and significant between D1 and D57 versus placebo ($p=0.0300$). For the facial seborrhoea, a tendency at D57 versus placebo is observed in favour of the probiotic, with a decrease in seborrhoea ($p=0.1735$).

3. *Malassezia* sp.:

The results illustrated by FIG. 4 show a significant decrease in *Malassezia* sp. for the product versus placebo from D15 ($p=0.0237$).

The change between D1 and D57 is significant for the active agent ($p=0.0272$) whereas there is no variation between D1 and D57 for the placebo.

One week after the treatment, at D64, the effectiveness of the product is maintained (tendency towards effect versus placebo, $p=0.2312$).

The following examples are examples of compositions useful for a process or an assembly in accordance with the invention.

Example 12

First Composition

Formulation of Coated Tablet Type

| Active material | mg/coated |
|---|---|
| *Lactobacillus paracasei* ST11 | $10^9$ cfu |
| *Lactobacillus johnsonii* | $10^9$ cfu |
| Excipient for the core of the | |
| Microcrystalline cellulose | 70 |
| Encompress ™ | 60 |

-continued

| Active material | mg/coated |
|---|---|
| Magnesium stearate | 3 |
| Anhydrous colloidal silica | 1 |
| Coating agent | |
| Shellac | 5 |
| Talc | 61 |
| Sucrose | 250 |
| Polyvinylpyrrolidone | 6 |
| Titanium dioxide | 0.3 |
| Colorant | 5 |

This type of coated tablet may be taken 1 to 3 times a day.

Second Composition

| Topical formulation | |
|---|---|
| | % by weight |
| Acrylates/C10-30 alkyl acrylate crosspolymer | 0.20% |
| Propylene glycol | 1.00% |
| Sodium laureth sulfate (3 mol at 28%) | 45.00 |
| Dimethicone PEG-7 avocadoate | 0.30% |
| Zinc pyridinethione | 0.40% |
| Triisopropanolamine | 0.25% |
| Deionized water | qs 100% |

Example 13

First Composition

| Scalp lotion | |
|---|---|
| | % by weight |
| *Lactobacillus paracasei* ST11 powder | 5.00 |
| Antioxidant | 0.05 |
| Isopropanol | 40.0 |
| Preserving agent | 0.30 |
| Water | qs 100% |

Second Composition

| Antidandruff shampoo | |
|---|---|
| | % by weight |
| Acrylates/C10-30 alkyl acrylate crosspolymer | 0.20% |
| Propylene glycol | 1.00% |
| Sodium laureth sulfate (3 mol at 28%) | 45.00 |
| Dimethicone PEG-7 avocadoate | 0.30% |
| zinc pyridinethione | 0.40% |
| Triisopropanolamine | 0.25% |
| Deionized water | qs 100% |

Example 14

First Composition

| Scalp care cream | |
|---|---|
| | % by weight |
| Arachidyl behenyl alcohol/arachidyl glucoside | 3.0% |
| Isohexadecane | 7.0% |
| *Lactobacillus paracasei* ST11 powder | 5.00% |
| Glycerol | 2.0% |
| *Vitreoscilla filiformis* extract | 3.0 |
| BHT | 0.05 |
| Methyl POB | 0.1 |
| Propyl POB | 0.05 |
| Water | qs 100% |

Second Composition

| Antidandruff lotion | |
|---|---|
| | % by weight |
| Acrylates/C10-30 alkyl acrylate crosspolymer | 0.20% |
| Propylene glycol | 1.00% |
| Ethanol | 60% |
| Dimethicone PEG-7 avocadoate | 0.30% |
| Octopirox | 1.00% |
| Triisopropanolamine | 0.25% |
| Deionized water | qs 100% |

Example 15

First Composition

| Scalp treating lotion | |
|---|---|
| | % by weight |
| *Bifidobacterium longum* lysate | 5.00** |
| Magnesium gluconate | 3.00 |
| Calcium lactate | 2.00 |
| Antioxidant | 0.05 |
| Isopropanol | 40.0 |
| Preserving agent | 0.30 |

Second Composition

| Antidandruff shampoo | |
|---|---|
| | % by weight |
| Acrylates/C10-30 alkyl acrylate crosspolymer | 0.20% |
| Propylene glycol | 1.00% |
| Sodium Laureth sulfate (3 mol at 28%) | 45.00 |
| Dimethicone PEG-7 avocadoate | 0.30% |
| Mixed oil of thyme and catnip | 1.00% |
| Zinc pyridinethione | 20% |
| Triisopropanolamine | 0.25% |
| Deionized water | qs 100% |

Example 16

Efficacy Study

Protocol

An assembly comprising a first oral composition based on probiotic microorganism (A) and a second topical composition based on zinc pyridinethione (B) was tested as regards its efficacy towards scalp dandruff relative to the administration of compositions (A) and (B) alone. The compositions have the following formulation:

A: $1 \times 10^9$ cfu/g of *Lactobacillus paracasei* ST11 NCC 2461 (CNCM I-2116)

B: shampoo containing 1% zinc pyridinethione

The treatment consists in administering daily via the oral route composition (A) as a single dose and via the topical route composition (B), over four weeks, and then composition (A) alone over a further four weeks. For comparative purposes, composition (A) is administered alone orally or composition (B) is administered alone topically over eight weeks.

This study was performed on 99 male adults aged between 18 and 60, who were identified following a clinical evaluation of their dandruff condition, classified from moderate to severe, with scores of greater than or equal to 3 (on a scale from 0 to 4) in the presence of squamae adhering to at least two quarters of the head, and of their scalp erythema.

In the clinical evaluation, the presence of erythema was also taken into account.

The 99 individuals were divided into three parallel groups of 33 individuals, with one group receiving compositions (A) and (B) and then composition (A) alone, one group receiving composition (A) alone and one group receiving composition (B) alone.

The effects of an assembly and of a process of the invention were tested and assessed by comparison of the three groups on D1, D15, D29, D43 and D57 by means of clinical evaluations performed on the following parameters: free dandruff, adherent squamae and erythema, and the overall score was calculated.

These evaluations were performed by qualified dermatologists according to the techniques usually used in the field.

Clinical Evaluation of the Scalp Dandruff (Scores)

At each visit, the dandruff condition, free dandruff and adherent squamae, was scored, for each item, by the investigator using a scale from 0 to 4 on each of the head quarters as follows:

0 absent
1 very mild
2 mild
3 moderate
4 severe

The sum of the scores for the head quarters as regards the free dandruff and the adherent squamae was calculated (and thus the scores for each of the two items could be between 0 and 16).

Clinical Evaluation of the Scalp Erythema

At each visit, the scalp erythema was scored by the investigator using a scale from 0 to 4 on each of the head quarters as follows:

0 absent
1 very mild
2 mild
3 moderate
4 severe

The sum of the scores for the head quarters was calculated (and thus the scores could be between 0 and 16).

Overall Clinical Score (Dandruff/Erythema Scores)

The overall clinical score is calculated by adding the scores for the free dandruff, adherent squamae and erythema.

The scores may be between 0 and 48. Thus, scores running from 13 to 9 are clinically advantageous, since a score of 9 corresponds to the score generally found in dandruff-free individuals (score of 3 for each of the items).

Results

The results (expressed as a total clinical score (TCS), corresponding to the score for free dandruff and adherent dandruff and for the erythema, show a significant improvement, from the first weeks of treatment, of the dandruff condition and the erythema of the scalp in the case of the individuals treated with the combination (A)+(B) and according to the process of the invention, relative to the individuals receiving composition (A) or (B) alone.

In particular, the efficacy of the antidandruff treatment is manifested from the very first days of treatment and lasts throughout the treatment with increased intensity, leading to a markedly improved clinical score.

On the other hand, administration of the probiotic alone is reflected by a clinical effect that is essentially manifested towards the final weeks of treatment, whereas the administration of the antidandruff active agent alone exerts an effect that is visible at the start of the treatment, but that ends up by vanishing quickly.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A cosmetic method for treating a scalp disorder, consisting of:
    administering an effective amount of a single probiotic microorganism of the *Lactobacillus paracasei* species and/or, a fraction thereof to a subject in need of such treatment.

2. The method according to claim 1, wherein the scalp disorder comprises a dandruff condition of the scalp.

3. The method according to claim 1, wherein the scalp disorder comprises discomfort of the scalp.

4. The method according to claim 1, wherein the scalp disorder comprises unbalanced ecoflora of the scalp.

5. The method according to claim 1, wherein the scalp disorder comprises compromised integrity of the barrier functions of the skin of the scalp.

6. The method according to claim 1, wherein the microorganism is administered topically or orally.

7. A cosmetic process for treating a dandruff condition of the scalp, consisting of:
    administering an effective amount of a first cosmetic active agent during a sequence consisting of a first period of time and a second consecutive period of time to a subject in need of such treatment, wherein the first period of time and the second period of time are not continuous; and
    administering at least one second cosmetic active agent, topically, during only one of either the first period of time or the second consecutive period of time to the subject;
    wherein:
    the first cosmetic active agent and the at least one second cosmetic active agent are formulated in separate compositions;
    the first cosmetic active agent consists of a probiotic *Lactobacillus paracasei*, and/or a fraction thereof; and
    the at least one second cosmetic active agent comprises at least one antidandruff active agent.

8. The process according to claim 7, wherein the first cosmetic active agent is administered orally or topically.

9. The process according to claim 7, wherein the at least one second cosmetic active agent is administered during the first period of time.

10. The process according to claim 7, wherein the sequence is repeated at least once.

11. The process according to claim 7, wherein the first period of time and second consecutive period of time are, independently of each other, from one to six weeks.

12. The process according to claim 7, wherein the dandruff condition of the scalp comprises dandruff in combination with: dryness of the scalp, hyperseborrhoea of the scalp, an imbalanced ecoflora, pruritus, inflammation of the scalp, or an imbalanced barrier function of the scalp.

13. The process according to claim 7, wherein the at least one second cosmetic active agent comprises at least one member selected from the group consisting of:
    a pyridinethione salt;
    a trihalocarbamide of formula (I), wherein Z represents a halogen atom or a $C_1$-$C_4$ trihaloalkyl group such as $CF_3$;

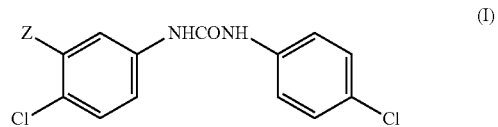

triclosan;
an azole compound;
an antifungal polymer;
a selenium sulfide;
sulfur in its various forms;
allantoin;
coal or wood tars and derivatives thereof;
salicylic acid;
undecylenic acid;
fumaric acid;
an allylamine and mixtures thereof;
ciclopirox;
octopirox;
piroctone olamine;
clobetasol propionate;
betamethasone valerate;
tea tree oil;
a mixed oil of thyme and catnip; and
a probiotic microorganism.

14. The process according to claim 7, wherein the at least one second cosmetic active agent comprises at least one member selected from the group consisting of zinc pyridinethione, salicylic acid, selenium disulfide, mixed oil of thyme and catnip, octopirox and a probiotic microorganism.

15. The process according to claim 7, wherein the second active agent is administered as a composition comprising the at least one second cosmetic active agent in an amount of from 0.001% to 10% by weight relative to a total weight of the composition.

16. A cosmetic assembly, consisting of:
a first cosmetic composition and a second cosmetic composition,
wherein:
the first cosmetic composition consists of an effective amount of a first cosmetic active agent consisting of *Lactobacillus paracasei*, and/or a fraction thereof;
the second composition comprises at least an effective amount of at least one second cosmetic active agent selected from antidandruff active agents for topical administration.

17. The assembly according to claim 16, wherein the second cosmetic active agent comprises at least one member selected from the group consisting of:
a pyridinethione salt;
a trihalocarbamide of formula (I), wherein Z represents a halogen atom or a $C_1$-$C_4$ trihaloalkyl group such as $CF_3$;

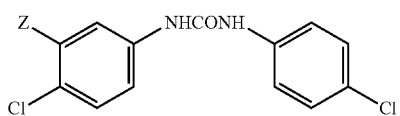

triclosan;
an azole compound;
an antifungal polymer;
a selenium sulfide;
sulfur in its various forms;
allantoin;
coal or wood tars and derivatives thereof;
salicylic acid;
undecylenic acid;
fumaric acid;
an allylamine and mixtures thereof;
ciclopirox;
octopirox;
piroctone olamine;
clobetasol propionate;
betamethasone valerate;
tea tree oil;
a mixed oil of thyme and catnip; and
a probiotic microorganism.

18. The assembly according to claim 16, wherein the first cosmetic composition is formulated in at least one form selected from the group consisting of a coated tablet, a gel capsule, a gel, an emulsion, a tablet, a capsule, a hydrogel, a food bar, a loose or compact powder, a liquid suspension or solution, a confectionery product, a fermented milk, a fermented cheese, chewing gum, toothpaste or a spray solution.

19. The assembly according to claim 16, wherein the at least one second composition comprises at least one member selected from the group consisting of a hair lotion, a shampoo, a hair conditioner, a detangler, a hair cream or gel, a styling lacquer, a hairsetting lotion, a treating lotion, a dye composition, a hair-restructuring lotion, a permanent-waving composition, a lotion or gel for combating hair loss, an antiparasitic shampoo or a medicated shampoo, and a scalp care product.

20. A cosmetic method for treating a dandruff condition of the scalp, consisting of:
administering an effective amount of a first cosmetic active agent and at least one second cosmetic active agent to a subject in need of such treatment;
wherein:
the first cosmetic active agent-consists of a single probiotic microorganism of the *Lactobacillus paracasei* species, and/or a fraction thereof; and
the at least one second active agent is selected from antidandruff active agents for topical administration.

21. A cosmetic method for treating a greasy scalp disorder, consisting of:
orally administering an effective amount of a single *Lactobacillus paracasei*, and/or a fraction thereof to a subject in need of such treatment.

22. The method according to claim 21, wherein the scalp disorder comprises a dandruff condition of the scalp.

23. The method according to claim 21, wherein the scalp disorder comprises discomfort of the scalp.

24. The method according to claim 21, wherein the scalp disorder comprises unbalanced ecoflora of the scalp.

25. The method according to claim 21, wherein the scalp disorder comprises compromised integrity of the barrier functions of the skin of the scalp.

26. A method for preparing an oral pharmaceutical or dermatological composition for treating inflammation of the greasy scalp, consisting of:
combining an effective amount of a single *Lactobacillus paracasei* and/or a fraction thereof with at least one pharmaceutical or dermatological excipient.

27. The method according to claim 26, wherein the scalp disorder comprises pruritis and/or seborrhoeic dermatitis of the scalp.

* * * * *